US012780878B2

(12) United States Patent
Chao et al.

(10) Patent No.: US 12,780,878 B2
(45) Date of Patent: Nov. 3, 2026

(54) CHIMERIC HEMAGGLUTININ PROTEIN AND A VACCINE COMPOSITION COMPRISING THE SAME

(71) Applicant: ACADEMIA SINICA, Taipei (TW)

(72) Inventors: Yu-Chan Chao, Taipei (TW); Chih-Hsuan Tsai, Taipei (TW); Chia-Jung Chang, Taipei (TW); Sung-Chan Wei, Taipei (TW); Lin-Li Liao, Taipei (TW); Huei-Ru Lo, Taipei (TW)

(73) Assignee: ACADEMIA SINICA, Taipei (TW)

( * ) Notice: Subject to any disclaimer, the term of this patent is extended or adjusted under 35 U.S.C. 154(b) by 337 days.

(21) Appl. No.: 17/627,212

(22) PCT Filed: Sep. 18, 2020

(86) PCT No.: PCT/US2020/051395

§ 371 (c)(1),
(2) Date: Jan. 14, 2022

(87) PCT Pub. No.: WO2021/055679

PCT Pub. Date: Mar. 25, 2021

(65) Prior Publication Data

US 2022/0267382 A1 Aug. 25, 2022

Related U.S. Application Data

(60) Provisional application No. 62/903,011, filed on Sep. 20, 2019, provisional application No. 62/904,014, filed on Sep. 23, 2019.

(51) Int. Cl.

| | |
|---|---|
| ***A61K 39/12*** | (2006.01) |
| ***A61P 31/16*** | (2006.01) |
| ***C07K 14/005*** | (2006.01) |
| *A61K 39/00* | (2006.01) |
| *C07K 14/11* | (2006.01) |

(52) U.S. Cl.

CPC ............ *C07K 14/005* (2013.01); *A61P 31/16* (2018.01); *A61K 39/00* (2013.01); *C07K 2319/00* (2013.01)

(58) Field of Classification Search

None

See application file for complete search history.

(56) References Cited

U.S. PATENT DOCUMENTS

| | | | |
|---|---|---|---|
| 10,131,695 | B2 | 11/2018 | Garcia-Sastre et al. |
| 10,272,148 | B2 | 4/2019 | Couture et al. |
| 2008/0014205 | A1 | 1/2008 | Horowitz et al. |
| 2013/0309248 | A1 | 11/2013 | Throsby et al. |
| 2015/0335729 | A1 | 11/2015 | Garcia-Sastre et al. |

FOREIGN PATENT DOCUMENTS

| | | | |
|---|---|---|---|
| JP | 2014-523254 | A | 9/2014 |
| KR | 10-1835989 | B1 | 3/2018 |

OTHER PUBLICATIONS

Scribbr (2025, 1 page, worldwideweb at scribbr.com) (Year: 2025).*
Perrie et al. (Int. J. Pharm. 2008, 364: 272-280) (Year: 2008).*
International Search Report, issued in PCT/US2020/051395, mailed Jan. 6, 2021, 8 pages.
Tsai et al., "Generation of Stable Influenza Virus Hemagglutinin through Structure-Guided Recombination", ACS Synthetic Biology, Sep. 30, 2019 (Online publication date), vol. 8, pp. A-K.
Written Opinion of the International Searching Authority, issued in PCT/US2020/051395, mailed Jan. 6, 2021, 7 pages.
Broecker et al., "A mosaic hemagglutinin-based influenza virus vaccine candidate protects mice from challenge with divergent H3N2 strains," npj Vaccines, vol. 4, No. 31, 2019, pp. 1-9.
Extended European Search Report for European Application No. 20865319.6, dated May 3, 2023, 14 pages.
Hai et al., "Influenza Viruses Expressing Chimeric Hemagglutinins: Globular Head and Stalk Domains Derived from Different Subtypes," Journal of Virology, vol. 86, No. 10, 2012, pp. 5774-5781.
Krammer et al., "Universal Influenza Virus Vaccines That Target the Conserved Hemagglutinin Stalk and Conserved Sites in the Head Domain," Journal of Infectious Diseases, vol. 219, 2019, pp. S62-S67.
Peng et al., "Protective efficacy of an inactivated chimeric H7/H5 avian influenza vaccine against highly pathogenic avian influenza H7N9 and clade 2.3.4.4 H5 viruses," Veterinary Microbiology, vol. 223, 2018, pp. 21-26.
Russell, "Acid-Induced Membrane Fusion by the Hemagglutinin Protein and Its Role in Influenza Virus Biology," Current Topics in Microbiology and Immunology, vol. 385, 2014, pp. 93-116.
Sautto et al., "Towards a universal influenza vaccine: different approaches for one goal," Virology Journal, vol. 15, No. 17, 2018, pp. 1-12.
Sriwilaijaroen et al., "Molecular basis of the structure and function of H1 hemagglutinin of influenza virus," Proceedings of the Japan Academy, Series B, vol. 88, No. 6, 2012, pp. 226-249.
Taiwanese Office Action and Search Report for Taiwanese Application No. 109132363, dated Apr. 13, 2022, 6 pages, considered English portions only.
"Influenza (seasonal)," World Health Organization (WHO), Jan. 31, 2018, 11 pages total.

(Continued)

*Primary Examiner* — Misook Yu
*Assistant Examiner* — Marianne Dibrino
(74) *Attorney, Agent, or Firm* — Birch, Stewart, Kolasch & Birch, LLP

(57) ABSTRACT

Provided is a chimeric hemagglutinin (HA) protein including an HA1 subunit and an HA2 subunit, in which the HA1 subunit is composed of a first domain derived from a parental HA1 subunit of a first subtype influenza virus and a second domain derived from a parental HA1 subunit of a second subtype influenza virus. The chimeric HA protein has improved thermal stability and can be used in a vaccine composition for preventing influenza virus infection. Also provided is a method of inducing an immune response against an influenza virus in a subject in need thereof that includes administering the chimeric HA protein to the subject, thereby conferring protection against the influenza virus infection on the subject.

5 Claims, 17 Drawing Sheets

Specification includes a Sequence Listing.

(56) References Cited

OTHER PUBLICATIONS

Bright et al., "Cross-Clade 15 Protective Immune Responses to Influenza Viruses with H5N1 HA and NA Elicited by an Influenza Virus-Like Particle," PLoS One, vol. 3, Issue 1, e1501, Jan. 30, 2008, pp. 1-14.
Chao et al., "A 2.9-Kilobase Noncoding Nuclear RNA Functions in the Establishment of Persistent Hz-1 Viral Infection," Journal of Virology, vol. 72, No. 3, Mar. 1998, pp. 2233-2245.
Cotter et al., "A Single Amino Acid in the Stalk Region of the H1N1pdm Influenza Virus HA Protein Affects Viral Fusion, Stability and Infectivity," PLoS Pathogens, vol. 10, Issue 1, e1003831, Jan. 2, 2014, pp. 1-9.
Farnsworth et al., "Antigenic stability of H1N1 pandemic vaccines correlates with vaccine strain," Vaccine, vol. 29, 2011, pp. 1529-1533.
Gao et al., "Human Infection with a Novel Avian-Origin Influenza A (H7N9) Virus," The New England Journal of Medicine, vol. 368, May 16, 2013, pp. 1888-1897.
Hanson et al., "Identification of Stabilizing Mutations in an H5 Hemagglutinin Influenza Virus Protein," Journal of Virology, vol. 90, No. 6, Mar. 2016, pp. 2981-2992.
Hu et al., "Antibody Immunity Induced by H7N9 Avian Influenza Vaccines: Evaluation Criteria, Affecting Factors, and Implications for Rational Vaccine Design," Frontiers in Microbiology, vol. 8, Article 1898, Sep. 26, 2017, pp. 1-9.
Khurana et al., "Bacterial HA1 Vaccine against Pandemic H5N1 Influenza Virus: Evidence of Oligomerization, Hemagglutination, and Cross-Protective Immunity in Ferrets," Journal of Virology, vol. 85, No. 3, Feb. 2011, pp. 1246-1256.
Mair et al., "Receptor binding and pH stability—How influenza A virus hemagglutinin affects host-specific virus infection," Biochimica et Biophysica Acta, vol. 1838, 2014, pp. 1153-1168.
Matrosovich et al., "Natural and synthetic sialic acid-containing inhibitors of influenza virus receptor binding," Reviews in Medical Virology, vol. 13, 2003, pp. 85-97.
Naik et al., "Baculovirus as an efficient vector for gene delivery into mosquitoes," Scientific Reports, vol. 8, No. 17778, 2018, pp. 1-14.
Nakowitsch et al., "Egg- or cell culture-derived hemagglutinin mutations impair virus stability and antigen content of inactivated influenza vaccines," Biotechnology Journal, vol. 9, 2014, pp. 405-414.
Nakowitsch et al., "Mutations affecting the stability of the haemagglutinin molecule impair the immunogenicity of live attenuated H3N2 intranasal influenza vaccine candidates lacking NS1," Vaccine, vol. 29, 2011, pp. 3517-3524.
Pei et al., "PROMALS3D: a tool for multiple protein sequence and structure alignments," Nucleic Acids Research, vol. 36, No. 7, 2008, pp. 2295-2300.
Sun et al., "A novel eight amino acid insertion contributes to the hemagglutinin cleavability and the virulence of a highly pathogenic avian influenza A (H7N3) virus in mice," Virology, vol. 488, 2016, pp. 120-128.
Tung et al., "Baculovirus IE2 Stimulates the Expression of Heat Shock Proteins in Insect and Mammalian Cells to Facilitate Its Proper Functioning." PLoS One, vol. 11, No. 2, e0148578, Feb. 10, 2016, pp. 1-24.
Wei et al., "Baculovirus IE2 Interacts with Viral DNA through Daxx to Generate an Organized Nuclear Body Structure for Gene Activation in Vero Cells," Journal of Virology, vol. 93, Issue 8, e00149-19, Apr. 3, 2019, pp. 1-22.
Weldon et al., "Enhanced Immunogenicity of Stabilized Trimeric Soluble Influenza Hemagglutinin," PLoS One, vol. 5, Issue 9, e12466, Sep. 1, 2010, pp. 1-8.
Xu et al., "Mutations of two transmembrane cysteines of hemagglutinin (HA) from influenza A H3N2 virus affect HA thermal stability and fusion activity," Virus Genes, vol. 47, 2013, pp. 20-26.
Yang et al., "Structural Analysis of the Hemagglutinin from the Recent 2013 H7N9 Influenza Virus." Journal of Virology, vol. 87, No. 22, Nov. 2013, pp. 12433-12446.
Yang et al., "Structure and receptor binding preferences of recombinant human A(H3N2) virus hemagglutinins," Virology, vol. 477, 2015, pp. 18-31.

* cited by examiner

SEQUENCE LISTING

```
<160> NUMBER OF SEQ ID NOS: 18

<210> SEQ ID NO 1
<211> LENGTH: 321
<212> TYPE: PRT
<213> ORGANISM: Influenza A virus

<400> SEQUENCE: 1

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Thr Asn Ile Pro Arg Ile Cys Ser Lys Gly Lys Arg Thr
        35                  40                  45

Val Asp Leu Gly Gln Cys Gly Leu Leu Gly Thr Ile Thr Gly Pro Pro
    50                  55                  60

Gln Cys Asp Gln Phe Leu Glu Phe Ser Ala Asp Leu Ile Ile Glu Arg
65                  70                  75                  80

Arg Glu Gly Ser Asp Val Cys Tyr Pro Gly Lys Phe Val Asn Glu Glu
                85                  90                  95

Ala Leu Arg Gln Ile Leu Arg Glu Ser Gly Gly Ile Asp Lys Glu Ala
            100                 105                 110

Met Gly Phe Thr Tyr Ser Gly Ile Arg Thr Asn Gly Ala Thr Ser Ala
        115                 120                 125

Cys Arg Arg Ser Gly Ser Ser Phe Tyr Ala Glu Met Lys Trp Leu Leu
    130                 135                 140

Ser Asn Thr Asp Asn Ala Ala Phe Pro Gln Met Thr Lys Ser Tyr Lys
145                 150                 155                 160

Asn Thr Arg Lys Ser Pro Ala Leu Ile Val Trp Gly Ile His His Ser
                165                 170                 175

Val Ser Thr Ala Glu Gln Thr Lys Leu Tyr Gly Ser Gly Asn Lys Leu
            180                 185                 190

Val Thr Val Gly Ser Ser Asn Tyr Gln Gln Ser Phe Val Pro Ser Pro
        195                 200                 205

Gly Ala Arg Pro Gln Val Asn Gly Leu Ser Gly Arg Ile Asp Phe His
    210                 215                 220

Trp Leu Met Leu Asn Pro Asn Asp Thr Val Thr Phe Ser Phe Asn Gly
225                 230                 235                 240

Ala Phe Ile Ala Pro Asp Arg Ala Ser Phe Leu Arg Gly Lys Ser Met
                245                 250                 255

Gly Ile Gln Ser Gly Val Gln Val Asp Ala Asn Cys Glu Gly Asp Cys
            260                 265                 270
```

```
Tyr His Ser Gly Gly Thr Ile Ile Ser Asn Leu Pro Phe Gln Asn Ile
        275                 280                 285

Asp Ser Arg Ala Val Gly Lys Cys Pro Arg Tyr Val Lys Gln Arg Ser
    290                 295                 300

Leu Leu Leu Ala Thr Gly Met Lys Asn Val Pro Glu Ile Pro Lys Gly
305                 310                 315                 320

Arg


<210> SEQ ID NO 2
<211> LENGTH: 329
<212> TYPE: PRT
<213> ORGANISM: Influenza A virus

<400> SEQUENCE: 2

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Thr Glu Gly Phe Thr Trp Thr
        115                 120                 125

Gly Val Thr Gln Asn Gly Gly Ser Asn Ala Cys Lys Arg Gly Pro Gly
    130                 135                 140

Ser Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Val His His Pro Ser Thr Asn Gln Glu Gln Thr
            180                 185                 190

Ser Leu Tyr Val Gln Ala Ser Gly Arg Val Thr Val Ser Thr Arg Arg
        195                 200                 205

Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Asp Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320
```

Arg Asn Val Pro Glu Lys Gln Thr Arg
325

<210> SEQ ID NO 3
<211> LENGTH: 319
<212> TYPE: PRT
<213> ORGANISM: Artificial Sequence
<220> FEATURE:
<223> OTHER INFORMATION: rA-HA1

<400> SEQUENCE: 3

Asp Lys Ile Cys Leu Gly His His Ala Val Ser Asn Gly Thr Lys Val
1 5 10 15

Asn Thr Leu Thr Glu Arg Gly Val Glu Val Val Asn Ala Thr Glu Thr
20 25 30

Val Glu Arg Thr Asn Ile Pro Arg Ile Cys Ser Lys Gly Lys Arg Thr
35 40 45

Val Asp Leu Gly Gln Cys Gly Leu Leu Gly Thr Ile Thr Gly Pro Pro
50 55 60

Gln Cys Asp Gln Phe Leu Glu Phe Ser Ala Asp Leu Ile Ile Glu Arg
65 70 75 80

Arg Glu Gly Ser Asp Val Cys Tyr Pro Gly Lys Phe Val Asn Glu Glu
85 90 95

Ala Leu Arg Gln Ile Leu Arg Glu Ser Gly Gly Ile Asp Lys Glu Ala
100 105 110

Met Gly Phe Thr Trp Thr Gly Val Thr Gln Asn Gly Ala Thr Ser Ala
115 120 125

Cys Arg Arg Ser Gly Ser Ser Phe Tyr Ala Glu Met Asn Trp Leu Thr
130 135 140

Lys Ser Gly Ser Thr Tyr Pro Val Leu Asn Val Ser Tyr Lys Asn Thr
145 150 155 160

Arg Lys Ser Pro Ala Leu Ile Val Trp Gly Ile His His Ser Val Ser
165 170 175

Thr Ala Glu Gln Thr Ser Leu Tyr Val Gln Ala Ser Gly Arg Val Thr
180 185 190

Val Gly Ser Ser Asn Tyr Gln Gln Thr Ile Ile Pro Ser Pro Gly Ala
195 200 205

Arg Pro Gln Val Asn Gly Leu Ser Gly Arg Ile Asp Phe His Trp Leu
210 215 220

Met Leu Asn Pro Asn Asp Thr Val Thr Ile Asn Ser Asn Gly Asn Leu
225 230 235 240

Ile Ala Pro Asp Arg Ala Ser Phe Leu Arg Gly Lys Ser Met Gly Ile
245 250 255

Gln Ser Gly Val Gln Val Asp Ala Asn Cys Glu Gly Asp Cys Tyr His
260 265 270

Ser Gly Gly Thr Ile Ile Ser Asn Leu Pro Phe Gln Asn Ile Asp Ser
275 280 285

Arg Ala Val Gly Lys Cys Pro Arg Tyr Val Lys Gln Arg Ser Leu Leu
290 295 300

Leu Ala Thr Gly Met Lys Asn Val Pro Glu Ile Pro Lys Gly Arg
305 310 315

<210> SEQ ID NO 4
<211> LENGTH: 321
<212> TYPE: PRT
<213> ORGANISM: Artificial Sequence
<220> FEATURE:

<223> OTHER INFORMATION: rB-HA1

<400> SEQUENCE: 4

Ala Thr Leu Cys Leu Gly His His Ala Val Pro Asn Gly Thr Leu Val
1 5 10 15

Lys Thr Ile Thr Asp Asp Gln Ile Glu Val Thr Asn Ala Thr Glu Leu
20 25 30

Val Gln Ser Thr Asn Ile Pro Arg Ile Cys Ser Lys Gly Lys Arg Thr
35 40 45

Val Asp Leu Gly Gln Cys Gly Leu Leu Gly Thr Ile Thr Gly Pro Pro
50 55 60

Gln Cys Asp Gln Phe Leu Glu Phe Ser Ala Asp Leu Ile Ile Glu Arg
65 70 75 80

Arg Glu Gly Ser Asp Val Cys Tyr Pro Gly Lys Phe Val Asn Glu Glu
85 90 95

Ala Leu Arg Gln Ile Leu Arg Glu Ser Gly Gly Ile Asp Lys Glu Ala
100 105 110

Met Gly Phe Thr Tyr Ser Gly Ile Arg Thr Asn Gly Ala Thr Ser Ala
115 120 125

Cys Arg Arg Ser Gly Ser Ser Phe Tyr Ala Glu Met Lys Trp Leu Leu
130 135 140

Ser Asn Thr Asp Asn Ala Ala Phe Pro Gln Met Thr Lys Ser Tyr Lys
145 150 155 160

Asn Thr Arg Lys Ser Pro Ala Leu Ile Val Trp Gly Ile His His Pro
165 170 175

Ser Thr Asn Gln Glu Gln Thr Lys Leu Tyr Gly Ser Gly Asn Lys Leu
180 185 190

Val Thr Val Gly Ser Ser Asn Tyr Gln Gln Ser Phe Val Pro Asn Ile
195 200 205

Gly Ser Arg Pro Gln Val Asn Gly Leu Ser Ser Arg Ile Asp Phe His
210 215 220

Trp Leu Met Leu Asn Pro Asn Asp Thr Val Thr Phe Ser Phe Asn Gly
225 230 235 240

Ala Phe Ile Ala Pro Asp Arg Ala Ser Phe Leu Arg Gly Lys Ser Met
245 250 255

Gly Ile Gln Ser Gly Val Gln Val Asp Ala Asn Cys Glu Gly Asp Cys
260 265 270

Tyr His Ser Gly Gly Thr Ile Pro Asn Asp Lys Pro Phe Gln Asn Ile
275 280 285

Asp Ser Arg Ala Val Gly Lys Cys Pro Arg Tyr Val Lys Gln Asn Thr
290 295 300

Leu Lys Leu Ala Thr Gly Met Arg Asn Val Pro Glu Ile Pro Lys Gly
305 310 315 320

Arg

<210> SEQ ID NO 5
<211> LENGTH: 320
<212> TYPE: PRT
<213> ORGANISM: Artificial Sequence
<220> FEATURE:
<223> OTHER INFORMATION: rC-HA1

<400> SEQUENCE: 5

Asp Lys Ile Cys Leu Gly His His Ala Val Ser Asn Gly Thr Lys Val
1 5 10 15

```
Asn Thr Leu Thr Glu Arg Gly Val Glu Val Val Asn Ala Thr Glu Thr
            20                  25                  30

Val Glu Arg Ser Ser Thr Gly Lys Ile Cys Asn Asn Pro His Arg Ile
        35                  40                  45

Val Asp Leu Gly Gln Cys Gly Leu Leu Gly Thr Ile Thr Gly Pro Pro
    50                  55                  60

Gln Cys Asp Gln Phe Leu Glu Phe Ser Ala Asp Leu Ile Ile Glu Arg
65                  70                  75                  80

Arg Glu Gly Ser Asp Val Cys Tyr Pro Gly Lys Phe Val Asn Glu Glu
                85                  90                  95

Ala Leu Arg Gln Ile Leu Arg Glu Ser Gly Gly Ile Asp Lys Glu Ala
            100                 105                 110

Met Gly Phe Thr Tyr Ser Gly Ile Arg Thr Asn Gly Ala Thr Ser Ala
        115                 120                 125

Cys Arg Arg Ser Gly Ser Ser Phe Tyr Ala Glu Met Lys Trp Leu Leu
    130                 135                 140

Ser Asn Thr Asp Asn Ala Ala Phe Pro Gln Met Thr Lys Ser Tyr Lys
145                 150                 155                 160

Asn Thr Arg Lys Ser Pro Ala Leu Ile Val Trp Gly Ile His His Ser
                165                 170                 175

Val Ser Thr Ala Glu Gln Thr Lys Leu Tyr Gly Ser Gly Asn Lys Leu
            180                 185                 190

Val Thr Val Gly Ser Ser Asn Tyr Gln Gln Ser Phe Val Pro Ser Pro
        195                 200                 205

Gly Ala Arg Pro Gln Val Asn Gly Leu Ser Gly Arg Ile Asp Phe His
    210                 215                 220

Trp Leu Met Leu Asn Pro Asn Asp Thr Val Thr Phe Ser Phe Asn Gly
225                 230                 235                 240

Ala Phe Ile Ala Pro Asp Arg Ala Ser Phe Leu Arg Gly Lys Ser Met
                245                 250                 255

Gly Met Arg Ser Asp Ala Pro Ile Asp Thr Cys Ile Ser Glu Cys Ile
            260                 265                 270

Thr Pro Asn Gly Ser Ile Ile Ser Asn Leu Pro Phe Gln Asn Val Asn
        275                 280                 285

Lys Ile Thr Tyr Gly Ala Cys Pro Lys Tyr Val Lys Gln Arg Ser Leu
    290                 295                 300

Leu Leu Ala Thr Gly Met Lys Asn Val Pro Glu Ile Pro Lys Gly Arg
305                 310                 315                 320
```

<210> SEQ ID NO 6
<211> LENGTH: 322
<212> TYPE: PRT
<213> ORGANISM: Artificial Sequence
<220> FEATURE:
<223> OTHER INFORMATION: rD-HA1

<400> SEQUENCE: 6

```
Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Thr Asn Ile Pro Arg Ile Cys Ser Lys Gly Lys Arg Thr
        35                  40                  45

Val Asp Leu Gly Gln Cys Gly Leu Leu Gly Thr Ile Thr Gly Pro Pro
    50                  55                  60
```

-continued

Gln Cys Asp Gln Phe Leu Glu Phe Ser Ala Asp Leu Ile Ile Glu Arg
65 70 75 80

Arg Glu Gly Ser Asp Val Cys Tyr Pro Gly Lys Phe Val Asn Glu Glu
85 90 95

Ala Leu Arg Gln Ile Leu Arg Glu Ser Gly Gly Ile Asp Lys Glu Ala
100 105 110

Met Gly Phe Thr Tyr Ser Gly Ile Arg Thr Asn Gly Gly Ser Asn Ala
115 120 125

Cys Lys Arg Gly Pro Gly Ser Asp Phe Tyr Ala Glu Met Lys Trp Leu
130 135 140

Leu Ser Asn Thr Asp Asn Ala Ala Phe Pro Gln Met Thr Lys Thr Met
145 150 155 160

Pro Asn Asn Asp Asn Phe Asp Lys Leu Tyr Val Trp Gly Ile His His
165 170 175

Ser Val Ser Thr Ala Glu Gln Thr Lys Leu Tyr Gly Ser Gly Asn Lys
180 185 190

Leu Val Thr Val Ser Thr Arg Arg Ser Gln Gln Ser Phe Val Pro Ser
195 200 205

Pro Gly Ala Arg Pro Trp Val Arg Gly Leu Ser Gly Arg Ile Asp Phe
210 215 220

His Trp Thr Ile Val Lys Pro Gly Asp Val Leu Val Phe Ser Phe Asn
225 230 235 240

Gly Ala Phe Ile Ala Pro Asp Arg Ala Ser Phe Leu Arg Gly Lys Ser
245 250 255

Met Gly Ile Gln Ser Gly Val Gln Val Asp Ala Asn Cys Glu Gly Asp
260 265 270

Cys Tyr His Ser Gly Gly Thr Ile Ile Ser Asn Leu Pro Phe Gln Asn
275 280 285

Ile Asp Ser Arg Ala Val Gly Lys Cys Pro Arg Tyr Val Lys Gln Arg
290 295 300

Ser Leu Leu Leu Ala Thr Gly Met Lys Asn Val Pro Glu Ile Pro Lys
305 310 315 320

Gly Arg

<210> SEQ ID NO 7
<211> LENGTH: 321
<212> TYPE: PRT
<213> ORGANISM: Artificial Sequence
<220> FEATURE:
<223> OTHER INFORMATION: rE-HA1

<400> SEQUENCE: 7

Asp Lys Ile Cys Leu Gly His His Ala Val Ser Asn Gly Thr Lys Val
1 5 10 15

Asn Thr Leu Thr Glu Arg Gly Val Glu Val Val Asn Ala Thr Glu Thr
20 25 30

Val Glu Arg Thr Asn Ile Pro Arg Ile Cys Ser Lys Gly Lys Arg Thr
35 40 45

Val Asp Leu Ile Asp Cys Thr Leu Ile Asp Ala Leu Leu Gly Asp Pro
50 55 60

His Cys Asp Gln Phe Leu Glu Phe Ser Ala Asp Leu Ile Ile Glu Arg
65 70 75 80

Ser Lys Ala Phe Ser Asn Cys Tyr Pro Tyr Asp Val Pro Asp Tyr Ala
85 90 95

```
Ser Leu Arg Gln Ile Leu Arg Glu Ser Gly Gly Ile Asp Lys Glu Ala
            100                 105                 110

Met Gly Phe Thr Tyr Ser Gly Ile Arg Thr Asn Gly Ala Thr Ser Ala
        115                 120                 125

Cys Arg Arg Ser Gly Ser Ser Phe Phe Ser Arg Leu Lys Trp Leu Leu
    130                 135                 140

Ser Asn Thr Asp Asn Ala Ala Phe Pro Gln Met Thr Lys Ser Tyr Lys
145                 150                 155                 160

Asn Thr Arg Lys Ser Pro Ala Leu Ile Ile Trp Gly Ile His His Ser
                165                 170                 175

Val Ser Thr Ala Glu Gln Thr Lys Leu Tyr Gly Ser Gly Asn Lys Leu
            180                 185                 190

Val Thr Val Gly Ser Ser Asn Tyr Gln Gln Ser Phe Val Pro Ser Pro
        195                 200                 205

Gly Ala Arg Pro Gln Val Asn Gly Leu Ser Gly Arg Ile Ser Ile Tyr
    210                 215                 220

Trp Leu Met Leu Asn Pro Asn Asp Thr Val Thr Phe Ser Phe Asn Gly
225                 230                 235                 240

Ala Phe Ile Ala Pro Asp Arg Ala Ser Phe Leu Arg Gly Lys Ser Met
                245                 250                 255

Gly Ile Gln Ser Gly Val Gln Val Asp Ala Asn Cys Glu Gly Asp Cys
            260                 265                 270

Tyr His Ser Gly Gly Thr Ile Ile Ser Asn Leu Pro Phe Gln Asn Ile
        275                 280                 285

Asp Ser Arg Ala Val Gly Lys Cys Pro Arg Tyr Val Lys Gln Arg Ser
    290                 295                 300

Leu Leu Leu Ala Thr Gly Met Lys Asn Val Pro Glu Ile Pro Lys Gly
305                 310                 315                 320

Arg


<210> SEQ ID NO 8
<211> LENGTH: 322
<212> TYPE: PRT
<213> ORGANISM: Artificial Sequence
<220> FEATURE:
<223> OTHER INFORMATION: rF-HA1

<400> SEQUENCE: 8

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Thr Asn Ile Pro Arg Ile Cys Ser Lys Gly Lys Arg Thr
        35                  40                  45

Leu Asp Gly Gly Gln Cys Gly Leu Leu Gly Thr Ile Thr Gly Pro Pro
    50                  55                  60

Gln Cys Asp Val Phe Gln Asn Glu Thr Trp Asp Leu Phe Val Glu Arg
65                  70                  75                  80

Arg Glu Gly Ser Asp Val Cys Tyr Pro Gly Lys Phe Val Asn Glu Glu
                85                  90                  95

Ala Leu Arg Ser Leu Val Ala Ser Ser Gly Thr Leu Glu Phe Ile Thr
            100                 105                 110

Glu Gly Phe Thr Tyr Ser Gly Ile Arg Thr Asn Gly Ala Thr Ser Ala
        115                 120                 125
```

-continued

Cys Arg Arg Ser Gly Ser Ser Phe Tyr Ala Glu Met Lys Trp Leu Leu
    130                 135                 140

Ser Asn Thr Asp Asn Ala Ala Phe Pro Gln Met Thr Lys Ser Tyr Lys
145                 150                 155                 160

Asn Thr Arg Lys Ser Pro Ala Leu Ile Val Trp Gly Ile His His Ser
                165                 170                 175

Val Ser Thr Ala Glu Gln Thr Lys Leu Tyr Gly Ser Gly Asn Lys Leu
            180                 185                 190

Val Thr Val Gly Ser Ser Asn Tyr Gln Gln Ser Phe Val Pro Ser Pro
        195                 200                 205

Gly Ala Arg Pro Gln Val Asn Gly Leu Ser Gly Arg Ile Asp Phe His
    210                 215                 220

Trp Leu Met Leu Asn Pro Asn Asp Thr Val Thr Phe Ser Phe Asn Gly
225                 230                 235                 240

Ala Phe Ile Ala Pro Arg Gly Tyr Phe Lys Met Arg Thr Gly Lys Ser
                245                 250                 255

Ser Ile Ile Gln Ser Gly Val Gln Val Asp Ala Asn Cys Glu Gly Asp
            260                 265                 270

Cys Tyr His Ser Gly Gly Thr Ile Ile Ser Asn Leu Pro Phe Gln Asn
        275                 280                 285

Ile Asp Ser Arg Ala Val Gly Lys Cys Pro Arg Tyr Val Lys Gln Arg
    290                 295                 300

Ser Leu Leu Leu Ala Thr Gly Met Lys Asn Val Pro Glu Ile Pro Lys
305                 310                 315                 320

Gly Arg

<210> SEQ ID NO 9
<211> LENGTH: 542
<212> TYPE: PRT
<213> ORGANISM: Influenza A virus

<400> SEQUENCE: 9

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Thr Asn Ile Pro Arg Ile Cys Ser Lys Gly Lys Arg Thr
        35                  40                  45

Val Asp Leu Gly Gln Cys Gly Leu Leu Gly Thr Ile Thr Gly Pro Pro
    50                  55                  60

Gln Cys Asp Gln Phe Leu Glu Phe Ser Ala Asp Leu Ile Ile Glu Arg
65                  70                  75                  80

Arg Glu Gly Ser Asp Val Cys Tyr Pro Gly Lys Phe Val Asn Glu Glu
                85                  90                  95

Ala Leu Arg Gln Ile Leu Arg Glu Ser Gly Gly Ile Asp Lys Glu Ala
            100                 105                 110

Met Gly Phe Thr Tyr Ser Gly Ile Arg Thr Asn Gly Ala Thr Ser Ala
        115                 120                 125

Cys Arg Arg Ser Gly Ser Ser Phe Tyr Ala Glu Met Lys Trp Leu Leu
    130                 135                 140

Ser Asn Thr Asp Asn Ala Ala Phe Pro Gln Met Thr Lys Ser Tyr Lys
145                 150                 155                 160

Asn Thr Arg Lys Ser Pro Ala Leu Ile Val Trp Gly Ile His His Ser
                165                 170                 175

```
Val Ser Thr Ala Glu Gln Thr Lys Leu Tyr Gly Ser Gly Asn Lys Leu
            180                 185                 190

Val Thr Val Gly Ser Ser Asn Tyr Gln Gln Ser Phe Val Pro Ser Pro
        195                 200                 205

Gly Ala Arg Pro Gln Val Asn Gly Leu Ser Gly Arg Ile Asp Phe His
    210                 215                 220

Trp Leu Met Leu Asn Pro Asn Asp Thr Val Thr Phe Ser Phe Asn Gly
225                 230                 235                 240

Ala Phe Ile Ala Pro Asp Arg Ala Ser Phe Leu Arg Gly Lys Ser Met
                245                 250                 255

Gly Ile Gln Ser Gly Val Gln Val Asp Ala Asn Cys Glu Gly Asp Cys
            260                 265                 270

Tyr His Ser Gly Gly Thr Ile Ile Ser Asn Leu Pro Phe Gln Asn Ile
        275                 280                 285

Asp Ser Arg Ala Val Gly Lys Cys Pro Arg Tyr Val Lys Gln Arg Ser
    290                 295                 300

Leu Leu Leu Ala Thr Gly Met Lys Asn Val Pro Glu Ile Pro Lys Gly
305                 310                 315                 320

Arg Gly Leu Phe Gly Ala Ile Ala Gly Phe Ile Glu Asn Gly Trp Glu
                325                 330                 335

Gly Leu Ile Asp Gly Trp Tyr Gly Phe Arg His Gln Asn Ala Gln Gly
            340                 345                 350

Glu Gly Thr Ala Ala Asp Tyr Lys Ser Thr Gln Ser Ala Ile Asp Gln
        355                 360                 365

Ile Thr Gly Lys Leu Asn Arg Leu Ile Glu Lys Thr Asn Gln Gln Phe
    370                 375                 380

Glu Leu Ile Asp Asn Glu Phe Asn Glu Val Glu Lys Gln Ile Gly Asn
385                 390                 395                 400

Val Ile Asn Trp Thr Arg Asp Ser Ile Thr Glu Val Trp Ser Tyr Asn
                405                 410                 415

Ala Glu Leu Leu Val Ala Met Glu Asn Gln His Thr Ile Asp Leu Ala
            420                 425                 430

Asp Ser Glu Met Asp Lys Leu Tyr Glu Arg Val Lys Arg Gln Leu Arg
        435                 440                 445

Glu Asn Ala Glu Glu Asp Gly Thr Gly Cys Phe Glu Ile Phe His Lys
    450                 455                 460

Cys Asp Asp Asp Cys Met Ala Ser Ile Arg Asn Asn Thr Tyr Asp His
465                 470                 475                 480

Ser Lys Tyr Arg Glu Glu Ala Met Gln Asn Arg Ile Gln Ile Asp Pro
                485                 490                 495

Val Lys Leu Ser Ser Gly Tyr Lys Asp Val Ile Leu Trp Phe Ser Phe
            500                 505                 510

Gly Ala Ser Cys Phe Ile Leu Leu Ala Ile Val Met Gly Leu Val Phe
        515                 520                 525

Ile Cys Val Lys Asn Gly Asn Met Arg Cys Thr Ile Cys Ile
    530                 535                 540


<210> SEQ ID NO 10
<211> LENGTH: 550
<212> TYPE: PRT
<213> ORGANISM: Influenza A virus

<400> SEQUENCE: 10

Gln Asp Leu Pro Gly Asn Asp Asn Ser Thr Ala Thr Leu Cys Leu Gly
1               5                   10                  15
```

```
His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Thr Glu Gly Phe Thr Trp Thr
        115                 120                 125

Gly Val Thr Gln Asn Gly Gly Ser Asn Ala Cys Lys Arg Gly Pro Gly
    130                 135                 140

Ser Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Val His His Pro Ser Thr Asn Gln Glu Gln Thr
            180                 185                 190

Ser Leu Tyr Val Gln Ala Ser Gly Arg Val Thr Val Ser Thr Arg Arg
        195                 200                 205

Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Asp Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr Arg Gly Leu Phe Gly Ala Ile Ala
                325                 330                 335

Gly Phe Ile Glu Asn Gly Trp Glu Gly Met Ile Asp Gly Trp Tyr Gly
            340                 345                 350

Phe Arg His Gln Asn Ser Glu Gly Thr Gly Gln Ala Ala Asp Leu Lys
        355                 360                 365

Ser Thr Gln Ala Ala Ile Asp Gln Ile Asn Gly Lys Leu Asn Arg Val
    370                 375                 380

Ile Glu Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430
```

```
Asn Gln His Thr Ile Asp Leu Thr Asp Ser Glu Met Asn Lys Leu Phe
        435                 440                 445

Glu Lys Thr Arg Arg Gln Leu Arg Glu Asn Ala Glu Asp Met Gly Asn
    450                 455                 460

Gly Cys Phe Lys Ile Tyr His Lys Cys Asp Asn Ala Cys Ile Glu Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Val Leu Leu Gly Phe Ile Met Trp Ala Cys Gln Arg Gly Asn Ile
    530                 535                 540

Arg Cys Asn Ile Cys Ile
545                 550


<210> SEQ ID NO 11
<211> LENGTH: 540
<212> TYPE: PRT
<213> ORGANISM: Artificial Sequence
<220> FEATURE:
<223> OTHER INFORMATION: FrA-HA

<400> SEQUENCE: 11

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Thr Asn Ile Pro Arg Ile Cys Ser Lys Gly Lys Arg Thr
        35                  40                  45

Val Asp Leu Gly Gln Cys Gly Leu Leu Gly Thr Ile Thr Gly Pro Pro
    50                  55                  60

Gln Cys Asp Gln Phe Leu Glu Phe Ser Ala Asp Leu Ile Ile Glu Arg
65                  70                  75                  80

Arg Glu Gly Ser Asp Val Cys Tyr Pro Gly Lys Phe Val Asn Glu Glu
                85                  90                  95

Ala Leu Arg Gln Ile Leu Arg Glu Ser Gly Gly Ile Asp Lys Glu Ala
            100                 105                 110

Met Gly Phe Thr Trp Thr Gly Val Thr Gln Asn Gly Ala Thr Ser Ala
        115                 120                 125

Cys Arg Arg Ser Gly Ser Ser Phe Tyr Ala Glu Met Asn Trp Leu Thr
    130                 135                 140

Lys Ser Gly Ser Thr Tyr Pro Val Leu Asn Val Ser Tyr Lys Asn Thr
145                 150                 155                 160

Arg Lys Ser Pro Ala Leu Ile Val Trp Gly Ile His His Ser Val Ser
                165                 170                 175

Thr Ala Glu Gln Thr Ser Leu Tyr Val Gln Ala Ser Gly Arg Val Thr
            180                 185                 190

Val Gly Ser Ser Asn Tyr Gln Gln Thr Ile Ile Pro Ser Pro Gly Ala
        195                 200                 205

Arg Pro Gln Val Asn Gly Leu Ser Gly Arg Ile Asp Phe His Trp Leu
    210                 215                 220

Met Leu Asn Pro Asn Asp Thr Val Thr Ile Asn Ser Asn Gly Asn Leu
225                 230                 235                 240
```

```
Ile Ala Pro Asp Arg Ala Ser Phe Leu Arg Gly Lys Ser Met Gly Ile
                245                 250                 255

Gln Ser Gly Val Gln Val Asp Ala Asn Cys Glu Gly Asp Cys Tyr His
            260                 265                 270

Ser Gly Gly Thr Ile Ile Ser Asn Leu Pro Phe Gln Asn Ile Asp Ser
        275                 280                 285

Arg Ala Val Gly Lys Cys Pro Arg Tyr Val Lys Gln Arg Ser Leu Leu
    290                 295                 300

Leu Ala Thr Gly Met Lys Asn Val Pro Glu Ile Pro Lys Gly Arg Gly
305                 310                 315                 320

Leu Phe Gly Ala Ile Ala Gly Phe Ile Glu Asn Gly Trp Glu Gly Leu
                325                 330                 335

Ile Asp Gly Trp Tyr Gly Phe Arg His Gln Asn Ala Gln Gly Glu Gly
            340                 345                 350

Thr Ala Ala Asp Tyr Lys Ser Thr Gln Ser Ala Ile Asp Gln Ile Thr
        355                 360                 365

Gly Lys Leu Asn Arg Leu Ile Glu Lys Thr Asn Gln Gln Phe Glu Leu
    370                 375                 380

Ile Asp Asn Glu Phe Asn Glu Val Glu Lys Gln Ile Gly Asn Val Ile
385                 390                 395                 400

Asn Trp Thr Arg Asp Ser Ile Thr Glu Val Trp Ser Tyr Asn Ala Glu
                405                 410                 415

Leu Leu Val Ala Met Glu Asn Gln His Thr Ile Asp Leu Ala Asp Ser
            420                 425                 430

Glu Met Asp Lys Leu Tyr Glu Arg Val Lys Arg Gln Leu Arg Glu Asn
        435                 440                 445

Ala Glu Glu Asp Gly Thr Gly Cys Phe Glu Ile Phe His Lys Cys Asp
    450                 455                 460

Asp Asp Cys Met Ala Ser Ile Arg Asn Asn Thr Tyr Asp His Ser Lys
465                 470                 475                 480

Tyr Arg Glu Glu Ala Met Gln Asn Arg Ile Gln Ile Asp Pro Val Lys
                485                 490                 495

Leu Ser Ser Gly Tyr Lys Asp Val Ile Leu Trp Phe Ser Phe Gly Ala
            500                 505                 510

Ser Cys Phe Ile Leu Leu Ala Ile Val Met Gly Leu Val Phe Ile Cys
        515                 520                 525

Val Lys Asn Gly Asn Met Arg Cys Thr Ile Cys Ile
    530                 535                 540


<210> SEQ ID NO 12
<211> LENGTH: 542
<212> TYPE: PRT
<213> ORGANISM: Artificial Sequence
<220> FEATURE:
<223> OTHER INFORMATION: FrB-HA

<400> SEQUENCE: 12

Ala Thr Leu Cys Leu Gly His His Ala Val Pro Asn Gly Thr Leu Val
1               5                   10                  15

Lys Thr Ile Thr Asp Asp Gln Ile Glu Val Thr Asn Ala Thr Glu Leu
            20                  25                  30

Val Gln Ser Thr Asn Ile Pro Arg Ile Cys Ser Lys Gly Lys Arg Thr
        35                  40                  45

Val Asp Leu Gly Gln Cys Gly Leu Leu Gly Thr Ile Thr Gly Pro Pro
    50                  55                  60
```

```
Gln Cys Asp Gln Phe Leu Glu Phe Ser Ala Asp Leu Ile Ile Glu Arg
65                  70                  75                  80

Arg Glu Gly Ser Asp Val Cys Tyr Pro Gly Lys Phe Val Asn Glu Glu
                85                  90                  95

Ala Leu Arg Gln Ile Leu Arg Glu Ser Gly Gly Ile Asp Lys Glu Ala
            100                 105                 110

Met Gly Phe Thr Tyr Ser Gly Ile Arg Thr Asn Gly Ala Thr Ser Ala
        115                 120                 125

Cys Arg Arg Ser Gly Ser Ser Phe Tyr Ala Glu Met Lys Trp Leu Leu
    130                 135                 140

Ser Asn Thr Asp Asn Ala Ala Phe Pro Gln Met Thr Lys Ser Tyr Lys
145                 150                 155                 160

Asn Thr Arg Lys Ser Pro Ala Leu Ile Val Trp Gly Ile His His Pro
                165                 170                 175

Ser Thr Asn Gln Glu Gln Thr Lys Leu Tyr Gly Ser Gly Asn Lys Leu
            180                 185                 190

Val Thr Val Gly Ser Ser Asn Tyr Gln Gln Ser Phe Val Pro Asn Ile
        195                 200                 205

Gly Ser Arg Pro Gln Val Asn Gly Leu Ser Ser Arg Ile Asp Phe His
    210                 215                 220

Trp Leu Met Leu Asn Pro Asn Asp Thr Val Thr Phe Ser Phe Asn Gly
225                 230                 235                 240

Ala Phe Ile Ala Pro Asp Arg Ala Ser Phe Leu Arg Gly Lys Ser Met
                245                 250                 255

Gly Ile Gln Ser Gly Val Gln Val Asp Ala Asn Cys Glu Gly Asp Cys
            260                 265                 270

Tyr His Ser Gly Gly Thr Ile Pro Asn Asp Lys Pro Phe Gln Asn Ile
        275                 280                 285

Asp Ser Arg Ala Val Gly Lys Cys Pro Arg Tyr Val Lys Gln Asn Thr
    290                 295                 300

Leu Lys Leu Ala Thr Gly Met Arg Asn Val Pro Glu Ile Pro Lys Gly
305                 310                 315                 320

Arg Gly Leu Phe Gly Ala Ile Ala Gly Phe Ile Glu Asn Gly Trp Glu
                325                 330                 335

Gly Leu Ile Asp Gly Trp Tyr Gly Phe Arg His Gln Asn Ala Gln Gly
            340                 345                 350

Glu Gly Thr Ala Ala Asp Tyr Lys Ser Thr Gln Ser Ala Ile Asp Gln
        355                 360                 365

Ile Thr Gly Lys Leu Asn Arg Leu Ile Glu Lys Thr Asn Gln Gln Phe
    370                 375                 380

Glu Leu Ile Asp Asn Glu Phe Asn Glu Val Glu Lys Gln Ile Gly Asn
385                 390                 395                 400

Val Ile Asn Trp Thr Arg Asp Ser Ile Thr Glu Val Trp Ser Tyr Asn
                405                 410                 415

Ala Glu Leu Leu Val Ala Met Glu Asn Gln His Thr Ile Asp Leu Ala
            420                 425                 430

Asp Ser Glu Met Asp Lys Leu Tyr Glu Arg Val Lys Arg Gln Leu Arg
        435                 440                 445

Glu Asn Ala Glu Glu Asp Gly Thr Gly Cys Phe Glu Ile Phe His Lys
    450                 455                 460

Cys Asp Asp Asp Cys Met Ala Ser Ile Arg Asn Asn Thr Tyr Asp His
465                 470                 475                 480
```

```
Ser Lys Tyr Arg Glu Glu Ala Met Gln Asn Arg Ile Gln Ile Asp Pro
                485                 490                 495

Val Lys Leu Ser Ser Gly Tyr Lys Asp Val Ile Leu Trp Phe Ser Phe
            500                 505                 510

Gly Ala Ser Cys Phe Ile Leu Leu Ala Ile Val Met Gly Leu Val Phe
        515                 520                 525

Ile Cys Val Lys Asn Gly Asn Met Arg Cys Thr Ile Cys Ile
    530                 535                 540


<210> SEQ ID NO 13
<211> LENGTH: 541
<212> TYPE: PRT
<213> ORGANISM: Artificial Sequence
<220> FEATURE:
<223> OTHER INFORMATION: FrC-HA

<400> SEQUENCE: 13

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Ser Ser Thr Gly Lys Ile Cys Asn Asn Pro His Arg Ile
        35                  40                  45

Val Asp Leu Gly Gln Cys Gly Leu Leu Gly Thr Ile Thr Gly Pro Pro
    50                  55                  60

Gln Cys Asp Gln Phe Leu Glu Phe Ser Ala Asp Leu Ile Ile Glu Arg
65                  70                  75                  80

Arg Glu Gly Ser Asp Val Cys Tyr Pro Gly Lys Phe Val Asn Glu Glu
                85                  90                  95

Ala Leu Arg Gln Ile Leu Arg Glu Ser Gly Gly Ile Asp Lys Glu Ala
            100                 105                 110

Met Gly Phe Thr Tyr Ser Gly Ile Arg Thr Asn Gly Ala Thr Ser Ala
        115                 120                 125

Cys Arg Arg Ser Gly Ser Ser Phe Tyr Ala Glu Met Lys Trp Leu Leu
    130                 135                 140

Ser Asn Thr Asp Asn Ala Ala Phe Pro Gln Met Thr Lys Ser Tyr Lys
145                 150                 155                 160

Asn Thr Arg Lys Ser Pro Ala Leu Ile Val Trp Gly Ile His His Ser
                165                 170                 175

Val Ser Thr Ala Glu Gln Thr Lys Leu Tyr Gly Ser Gly Asn Lys Leu
            180                 185                 190

Val Thr Val Gly Ser Ser Asn Tyr Gln Gln Ser Phe Val Pro Ser Pro
        195                 200                 205

Gly Ala Arg Pro Gln Val Asn Gly Leu Ser Gly Arg Ile Asp Phe His
    210                 215                 220

Trp Leu Met Leu Asn Pro Asn Asp Thr Val Thr Phe Ser Phe Asn Gly
225                 230                 235                 240

Ala Phe Ile Ala Pro Asp Arg Ala Ser Phe Leu Arg Gly Lys Ser Met
                245                 250                 255

Gly Met Arg Ser Asp Ala Pro Ile Asp Thr Cys Ile Ser Glu Cys Ile
            260                 265                 270

Thr Pro Asn Gly Ser Ile Ile Ser Asn Leu Pro Phe Gln Asn Val Asn
        275                 280                 285

Lys Ile Thr Tyr Gly Ala Cys Pro Lys Tyr Val Lys Gln Arg Ser Leu
    290                 295                 300
```

Leu Leu Ala Thr Gly Met Lys Asn Val Pro Glu Ile Pro Lys Gly Arg
305 310 315 320

Gly Leu Phe Gly Ala Ile Ala Gly Phe Ile Glu Asn Gly Trp Glu Gly
325 330 335

Leu Ile Asp Gly Trp Tyr Gly Phe Arg His Gln Asn Ala Gln Gly Glu
340 345 350

Gly Thr Ala Ala Asp Tyr Lys Ser Thr Gln Ser Ala Ile Asp Gln Ile
355 360 365

Thr Gly Lys Leu Asn Arg Leu Ile Glu Lys Thr Asn Gln Gln Phe Glu
370 375 380

Leu Ile Asp Asn Glu Phe Asn Glu Val Glu Lys Gln Ile Gly Asn Val
385 390 395 400

Ile Asn Trp Thr Arg Asp Ser Ile Thr Glu Val Trp Ser Tyr Asn Ala
405 410 415

Glu Leu Leu Val Ala Met Glu Asn Gln His Thr Ile Asp Leu Ala Asp
420 425 430

Ser Glu Met Asp Lys Leu Tyr Glu Arg Val Lys Arg Gln Leu Arg Glu
435 440 445

Asn Ala Glu Glu Asp Gly Thr Gly Cys Phe Glu Ile Phe His Lys Cys
450 455 460

Asp Asp Asp Cys Met Ala Ser Ile Arg Asn Asn Thr Tyr Asp His Ser
465 470 475 480

Lys Tyr Arg Glu Glu Ala Met Gln Asn Arg Ile Gln Ile Asp Pro Val
485 490 495

Lys Leu Ser Ser Gly Tyr Lys Asp Val Ile Leu Trp Phe Ser Phe Gly
500 505 510

Ala Ser Cys Phe Ile Leu Leu Ala Ile Val Met Gly Leu Val Phe Ile
515 520 525

Cys Val Lys Asn Gly Asn Met Arg Cys Thr Ile Cys Ile
530 535 540

<210> SEQ ID NO 14
<211> LENGTH: 543
<212> TYPE: PRT
<213> ORGANISM: Artificial Sequence
<220> FEATURE:
<223> OTHER INFORMATION: FrD-HA

<400> SEQUENCE: 14

Asp Lys Ile Cys Leu Gly His His Ala Val Ser Asn Gly Thr Lys Val
1 5 10 15

Asn Thr Leu Thr Glu Arg Gly Val Glu Val Val Asn Ala Thr Glu Thr
20 25 30

Val Glu Arg Thr Asn Ile Pro Arg Ile Cys Ser Lys Gly Lys Arg Thr
35 40 45

Val Asp Leu Gly Gln Cys Gly Leu Leu Gly Thr Ile Thr Gly Pro Pro
50 55 60

Gln Cys Asp Gln Phe Leu Glu Phe Ser Ala Asp Leu Ile Ile Glu Arg
65 70 75 80

Arg Glu Gly Ser Asp Val Cys Tyr Pro Gly Lys Phe Val Asn Glu Glu
85 90 95

Ala Leu Arg Gln Ile Leu Arg Glu Ser Gly Gly Ile Asp Lys Glu Ala
100 105 110

Met Gly Phe Thr Tyr Ser Gly Ile Arg Thr Asn Gly Gly Ser Asn Ala
115 120 125

```
Cys Lys Arg Gly Pro Gly Ser Asp Phe Tyr Ala Glu Met Lys Trp Leu
    130                 135                 140

Leu Ser Asn Thr Asp Asn Ala Ala Phe Pro Gln Met Thr Lys Thr Met
145                 150                 155                 160

Pro Asn Asn Asp Asn Phe Asp Lys Leu Tyr Val Trp Gly Ile His His
                165                 170                 175

Ser Val Ser Thr Ala Glu Gln Thr Lys Leu Tyr Gly Ser Gly Asn Lys
            180                 185                 190

Leu Val Thr Val Ser Thr Arg Arg Ser Gln Gln Ser Phe Val Pro Ser
        195                 200                 205

Pro Gly Ala Arg Pro Trp Val Arg Gly Leu Ser Gly Arg Ile Asp Phe
    210                 215                 220

His Trp Thr Ile Val Lys Pro Gly Asp Val Leu Val Phe Ser Phe Asn
225                 230                 235                 240

Gly Ala Phe Ile Ala Pro Asp Arg Ala Ser Phe Leu Arg Gly Lys Ser
                245                 250                 255

Met Gly Ile Gln Ser Gly Val Gln Val Asp Ala Asn Cys Glu Gly Asp
            260                 265                 270

Cys Tyr His Ser Gly Gly Thr Ile Ile Ser Asn Leu Pro Phe Gln Asn
        275                 280                 285

Ile Asp Ser Arg Ala Val Gly Lys Cys Pro Arg Tyr Val Lys Gln Arg
    290                 295                 300

Ser Leu Leu Leu Ala Thr Gly Met Lys Asn Val Pro Glu Ile Pro Lys
305                 310                 315                 320

Gly Arg Gly Leu Phe Gly Ala Ile Ala Gly Phe Ile Glu Asn Gly Trp
                325                 330                 335

Glu Gly Leu Ile Asp Gly Trp Tyr Gly Phe Arg His Gln Asn Ala Gln
            340                 345                 350

Gly Glu Gly Thr Ala Ala Asp Tyr Lys Ser Thr Gln Ser Ala Ile Asp
        355                 360                 365

Gln Ile Thr Gly Lys Leu Asn Arg Leu Ile Glu Lys Thr Asn Gln Gln
    370                 375                 380

Phe Glu Leu Ile Asp Asn Glu Phe Asn Glu Val Glu Lys Gln Ile Gly
385                 390                 395                 400

Asn Val Ile Asn Trp Thr Arg Asp Ser Ile Thr Glu Val Trp Ser Tyr
                405                 410                 415

Asn Ala Glu Leu Leu Val Ala Met Glu Asn Gln His Thr Ile Asp Leu
            420                 425                 430

Ala Asp Ser Glu Met Asp Lys Leu Tyr Glu Arg Val Lys Arg Gln Leu
        435                 440                 445

Arg Glu Asn Ala Glu Glu Asp Gly Thr Gly Cys Phe Glu Ile Phe His
    450                 455                 460

Lys Cys Asp Asp Asp Cys Met Ala Ser Ile Arg Asn Asn Thr Tyr Asp
465                 470                 475                 480

His Ser Lys Tyr Arg Glu Glu Ala Met Gln Asn Arg Ile Gln Ile Asp
                485                 490                 495

Pro Val Lys Leu Ser Ser Gly Tyr Lys Asp Val Ile Leu Trp Phe Ser
            500                 505                 510

Phe Gly Ala Ser Cys Phe Ile Leu Leu Ala Ile Val Met Gly Leu Val
        515                 520                 525

Phe Ile Cys Val Lys Asn Gly Asn Met Arg Cys Thr Ile Cys Ile
    530                 535                 540
```

<210> SEQ ID NO 15
<211> LENGTH: 542
<212> TYPE: PRT
<213> ORGANISM: Artificial Sequence
<220> FEATURE:
<223> OTHER INFORMATION: FrE-HA

<400> SEQUENCE: 15

```
Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Thr Asn Ile Pro Arg Ile Cys Ser Lys Gly Lys Arg Thr
        35                  40                  45

Val Asp Leu Ile Asp Cys Thr Leu Ile Asp Ala Leu Leu Gly Asp Pro
    50                  55                  60

His Cys Asp Gln Phe Leu Glu Phe Ser Ala Asp Leu Ile Ile Glu Arg
65                  70                  75                  80

Ser Lys Ala Phe Ser Asn Cys Tyr Pro Tyr Asp Val Pro Asp Tyr Ala
                85                  90                  95

Ser Leu Arg Gln Ile Leu Arg Glu Ser Gly Gly Ile Asp Lys Glu Ala
            100                 105                 110

Met Gly Phe Thr Tyr Ser Gly Ile Arg Thr Asn Gly Ala Thr Ser Ala
        115                 120                 125

Cys Arg Arg Ser Gly Ser Ser Phe Phe Ser Arg Leu Lys Trp Leu Leu
    130                 135                 140

Ser Asn Thr Asp Asn Ala Ala Phe Pro Gln Met Thr Lys Ser Tyr Lys
145                 150                 155                 160

Asn Thr Arg Lys Ser Pro Ala Leu Ile Ile Trp Gly Ile His His Ser
                165                 170                 175

Val Ser Thr Ala Glu Gln Thr Lys Leu Tyr Gly Ser Gly Asn Lys Leu
            180                 185                 190

Val Thr Val Gly Ser Ser Asn Tyr Gln Gln Ser Phe Val Pro Ser Pro
        195                 200                 205

Gly Ala Arg Pro Gln Val Asn Gly Leu Ser Gly Arg Ile Ser Ile Tyr
    210                 215                 220

Trp Leu Met Leu Asn Pro Asn Asp Thr Val Thr Phe Ser Phe Asn Gly
225                 230                 235                 240

Ala Phe Ile Ala Pro Asp Arg Ala Ser Phe Leu Arg Gly Lys Ser Met
                245                 250                 255

Gly Ile Gln Ser Gly Val Gln Val Asp Ala Asn Cys Glu Gly Asp Cys
            260                 265                 270

Tyr His Ser Gly Gly Thr Ile Ile Ser Asn Leu Pro Phe Gln Asn Ile
        275                 280                 285

Asp Ser Arg Ala Val Gly Lys Cys Pro Arg Tyr Val Lys Gln Arg Ser
    290                 295                 300

Leu Leu Leu Ala Thr Gly Met Lys Asn Val Pro Glu Ile Pro Lys Gly
305                 310                 315                 320

Arg Gly Leu Phe Gly Ala Ile Ala Gly Phe Ile Glu Asn Gly Trp Glu
                325                 330                 335

Gly Leu Ile Asp Gly Trp Tyr Gly Phe Arg His Gln Asn Ala Gln Gly
            340                 345                 350

Glu Gly Thr Ala Ala Asp Tyr Lys Ser Thr Gln Ser Ala Ile Asp Gln
        355                 360                 365
```

```
Ile Thr Gly Lys Leu Asn Arg Leu Ile Glu Lys Thr Asn Gln Gln Phe
    370                 375                 380

Glu Leu Ile Asp Asn Glu Phe Asn Glu Val Glu Lys Gln Ile Gly Asn
385                 390                 395                 400

Val Ile Asn Trp Thr Arg Asp Ser Ile Thr Glu Val Trp Ser Tyr Asn
                405                 410                 415

Ala Glu Leu Leu Val Ala Met Glu Asn Gln His Thr Ile Asp Leu Ala
            420                 425                 430

Asp Ser Glu Met Asp Lys Leu Tyr Glu Arg Val Lys Arg Gln Leu Arg
        435                 440                 445

Glu Asn Ala Glu Glu Asp Gly Thr Gly Cys Phe Glu Ile Phe His Lys
    450                 455                 460

Cys Asp Asp Asp Cys Met Ala Ser Ile Arg Asn Asn Thr Tyr Asp His
465                 470                 475                 480

Ser Lys Tyr Arg Glu Glu Ala Met Gln Asn Arg Ile Gln Ile Asp Pro
                485                 490                 495

Val Lys Leu Ser Ser Gly Tyr Lys Asp Val Ile Leu Trp Phe Ser Phe
            500                 505                 510

Gly Ala Ser Cys Phe Ile Leu Leu Ala Ile Val Met Gly Leu Val Phe
        515                 520                 525

Ile Cys Val Lys Asn Gly Asn Met Arg Cys Thr Ile Cys Ile
    530                 535                 540


<210> SEQ ID NO 16
<211> LENGTH: 543
<212> TYPE: PRT
<213> ORGANISM: Artificial Sequence
<220> FEATURE:
<223> OTHER INFORMATION: FrF-HA

<400> SEQUENCE: 16

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Thr Asn Ile Pro Arg Ile Cys Ser Lys Gly Lys Arg Thr
        35                  40                  45

Leu Asp Gly Gly Gln Cys Gly Leu Leu Gly Thr Ile Thr Gly Pro Pro
    50                  55                  60

Gln Cys Asp Val Phe Gln Asn Glu Thr Trp Asp Leu Phe Val Glu Arg
65                  70                  75                  80

Arg Glu Gly Ser Asp Val Cys Tyr Pro Gly Lys Phe Val Asn Glu Glu
                85                  90                  95

Ala Leu Arg Ser Leu Val Ala Ser Ser Gly Thr Leu Glu Phe Ile Thr
            100                 105                 110

Glu Gly Phe Thr Tyr Ser Gly Ile Arg Thr Asn Gly Ala Thr Ser Ala
        115                 120                 125

Cys Arg Arg Ser Gly Ser Ser Phe Tyr Ala Glu Met Lys Trp Leu Leu
    130                 135                 140

Ser Asn Thr Asp Asn Ala Ala Phe Pro Gln Met Thr Lys Ser Tyr Lys
145                 150                 155                 160

Asn Thr Arg Lys Ser Pro Ala Leu Ile Val Trp Gly Ile His His Ser
                165                 170                 175

Val Ser Thr Ala Glu Gln Thr Lys Leu Tyr Gly Ser Gly Asn Lys Leu
            180                 185                 190
```

```
Val Thr Val Gly Ser Ser Asn Tyr Gln Gln Ser Phe Val Pro Ser Pro
        195                 200                 205

Gly Ala Arg Pro Gln Val Asn Gly Leu Ser Gly Arg Ile Asp Phe His
    210                 215                 220

Trp Leu Met Leu Asn Pro Asn Asp Thr Val Thr Phe Ser Phe Asn Gly
225                 230                 235                 240

Ala Phe Ile Ala Pro Arg Gly Tyr Phe Lys Met Arg Thr Gly Lys Ser
                245                 250                 255

Ser Ile Ile Gln Ser Gly Val Gln Val Asp Ala Asn Cys Glu Gly Asp
            260                 265                 270

Cys Tyr His Ser Gly Gly Thr Ile Ile Ser Asn Leu Pro Phe Gln Asn
        275                 280                 285

Ile Asp Ser Arg Ala Val Gly Lys Cys Pro Arg Tyr Val Lys Gln Arg
    290                 295                 300

Ser Leu Leu Leu Ala Thr Gly Met Lys Asn Val Pro Glu Ile Pro Lys
305                 310                 315                 320

Gly Arg Gly Leu Phe Gly Ala Ile Ala Gly Phe Ile Glu Asn Gly Trp
                325                 330                 335

Glu Gly Leu Ile Asp Gly Trp Tyr Gly Phe Arg His Gln Asn Ala Gln
            340                 345                 350

Gly Glu Gly Thr Ala Ala Asp Tyr Lys Ser Thr Gln Ser Ala Ile Asp
        355                 360                 365

Gln Ile Thr Gly Lys Leu Asn Arg Leu Ile Glu Lys Thr Asn Gln Gln
    370                 375                 380

Phe Glu Leu Ile Asp Asn Glu Phe Asn Glu Val Glu Lys Gln Ile Gly
385                 390                 395                 400

Asn Val Ile Asn Trp Thr Arg Asp Ser Ile Thr Glu Val Trp Ser Tyr
                405                 410                 415

Asn Ala Glu Leu Leu Val Ala Met Glu Asn Gln His Thr Ile Asp Leu
            420                 425                 430

Ala Asp Ser Glu Met Asp Lys Leu Tyr Glu Arg Val Lys Arg Gln Leu
        435                 440                 445

Arg Glu Asn Ala Glu Glu Asp Gly Thr Gly Cys Phe Glu Ile Phe His
    450                 455                 460

Lys Cys Asp Asp Asp Cys Met Ala Ser Ile Arg Asn Asn Thr Tyr Asp
465                 470                 475                 480

His Ser Lys Tyr Arg Glu Glu Ala Met Gln Asn Arg Ile Gln Ile Asp
                485                 490                 495

Pro Val Lys Leu Ser Ser Gly Tyr Lys Asp Val Ile Leu Trp Phe Ser
            500                 505                 510

Phe Gly Ala Ser Cys Phe Ile Leu Leu Ala Ile Val Met Gly Leu Val
        515                 520                 525

Phe Ile Cys Val Lys Asn Gly Asn Met Arg Cys Thr Ile Cys Ile
    530                 535                 540


<210> SEQ ID NO 17
<211> LENGTH: 320
<212> TYPE: PRT
<213> ORGANISM: Influenza A virus

<400> SEQUENCE: 17

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30
```

```
Val Glu Arg Thr Asn Ile Pro Arg Ile Cys Ser Lys Gly Lys Arg Thr
        35                  40                  45

Val Asp Leu Gly Gln Cys Gly Leu Leu Gly Thr Ile Thr Gly Pro Pro
    50                  55                  60

Gln Cys Asp Gln Phe Leu Glu Phe Ser Ala Asp Leu Ile Ile Glu Arg
65                  70                  75                  80

Arg Glu Gly Ser Asp Val Cys Tyr Pro Gly Lys Phe Val Asn Glu Glu
                85                  90                  95

Ala Leu Arg Gln Ile Leu Arg Glu Ser Gly Gly Ile Asp Lys Glu Ala
            100                 105                 110

Met Gly Phe Thr Tyr Ser Gly Ile Arg Thr Asn Gly Ala Thr Ser Ala
        115                 120                 125

Cys Arg Arg Ser Gly Ser Ser Phe Tyr Ala Glu Met Lys Trp Leu Leu
    130                 135                 140

Ser Asn Thr Asp Asn Ala Ala Phe Pro Gln Met Thr Lys Ser Tyr Lys
145                 150                 155                 160

Asn Thr Arg Lys Ser Pro Ala Leu Ile Val Trp Gly Ile His His Ser
                165                 170                 175

Val Ser Thr Ala Glu Gln Thr Lys Leu Tyr Gly Ser Gly Asn Lys Leu
            180                 185                 190

Val Thr Val Gly Ser Ser Asn Tyr Gln Gln Ser Phe Val Pro Ser Pro
        195                 200                 205

Gly Ala Arg Pro Gln Val Asn Gly Leu Ser Gly Arg Ile Asp Phe His
    210                 215                 220

Trp Leu Met Leu Asn Pro Asn Asp Thr Val Thr Phe Ser Phe Asn Gly
225                 230                 235                 240

Ala Phe Ile Ala Pro Asp Arg Ala Ser Phe Leu Arg Gly Lys Ser Met
                245                 250                 255

Gly Ile Gln Ser Gly Val Gln Val Asp Ala Asn Cys Glu Gly Asp Cys
            260                 265                 270

Tyr His Ser Gly Gly Thr Ile Ile Ser Asn Leu Pro Phe Gln Asn Ile
        275                 280                 285

Asp Ser Arg Ala Val Gly Lys Cys Pro Arg Tyr Val Lys Gln Arg Ser
    290                 295                 300

Leu Leu Leu Ala Thr Gly Met Lys Asn Val Pro Glu Ile Pro Lys Gly
305                 310                 315                 320
```

```
<210> SEQ ID NO 18
<211> LENGTH: 319
<212> TYPE: PRT
<213> ORGANISM: Influenza A virus

<400> SEQUENCE: 18

Ala Thr Leu Cys Leu Gly His His Ala Val Pro Asn Gly Thr Leu Val
1               5                   10                  15

Lys Thr Ile Thr Asp Asp Gln Ile Glu Val Thr Asn Ala Thr Glu Leu
            20                  25                  30

Val Gln Ser Ser Ser Thr Gly Lys Ile Cys Asn Asn Pro His Arg Ile
        35                  40                  45

Leu Asp Gly Ile Asp Cys Thr Leu Ile Asp Ala Leu Leu Gly Asp Pro
    50                  55                  60

His Cys Asp Val Phe Gln Asn Glu Thr Trp Asp Leu Phe Val Glu Arg
65                  70                  75                  80
```

-continued

```
Ser Lys Ala Phe Ser Asn Cys Tyr Pro Tyr Asp Val Pro Asp Tyr Ala
                85                  90                  95

Ser Leu Arg Ser Leu Val Ala Ser Ser Gly Thr Leu Glu Phe Ile Thr
            100                 105                 110

Glu Gly Phe Thr Trp Thr Gly Val Thr Gln Asn Gly Gly Ser Asn Ala
        115                 120                 125

Cys Lys Arg Gly Pro Gly Ser Gly Phe Phe Ser Arg Leu Asn Trp Leu
    130                 135                 140

Thr Lys Ser Gly Ser Thr Tyr Pro Val Leu Asn Val Thr Met Pro Asn
145                 150                 155                 160

Asn Asp Asn Phe Asp Lys Leu Tyr Ile Trp Gly Val His His Pro Ser
                165                 170                 175

Thr Asn Gln Glu Gln Thr Ser Leu Tyr Val Gln Ala Ser Gly Arg Val
            180                 185                 190

Thr Val Ser Thr Arg Arg Ser Gln Gln Thr Ile Ile Pro Asn Ile Gly
        195                 200                 205

Ser Arg Pro Trp Val Arg Gly Leu Ser Ser Arg Ile Ser Ile Tyr Trp
    210                 215                 220

Thr Ile Val Lys Pro Gly Asp Val Leu Val Ile Asn Ser Asn Gly Asn
225                 230                 235                 240

Leu Ile Ala Pro Arg Gly Tyr Phe Lys Met Arg Thr Gly Lys Ser Ser
                245                 250                 255

Ile Met Arg Ser Asp Ala Pro Ile Asp Thr Cys Ile Ser Glu Cys Ile
            260                 265                 270

Thr Pro Asn Gly Ser Ile Pro Asn Asp Lys Pro Phe Gln Asn Val Asn
        275                 280                 285

Lys Ile Thr Tyr Gly Ala Cys Pro Lys Tyr Val Lys Gln Asn Thr Leu
    290                 295                 300

Lys Leu Ala Thr Gly Met Arg Asn Val Pro Glu Lys Gln Thr Arg
305                 310                 315
```

CHIMERIC HEMAGGLUTININ PROTEIN AND A VACCINE COMPOSITION COMPRISING THE SAME

CROSS REFERENCE TO RELATED APPLICATIONS

This application is the National Phase of PCT International Application No. PCT/US2020/051395, filed on Sep. 18, 2020, which claims priority under 35 U.S.C. 119(e) to U.S. Provisional Application No. 62/903,011, filed on Sep. 20, 2019 and 62/904,014, filed on Sep. 23, 2019, all of which are hereby expressly incorporated by reference into the present application.

REFERENCE TO ELECTRONIC SEQUENCE LISTING

This application includes an electronically submitted sequence listing in .txt format. The .txt file contains a sequence listing entitled "21P0587_supplement seq list .txt" created on May 2, 2025 and is 66,307 bytes in size. The sequence listing contained in this .txt file is part of the specification and is hereby incorporated by reference herein in its entirety.

BACKGROUND

1. Technical Field

The present disclosure relates to a chimeric hemagglutinin (HA) protein exhibiting high stability and immunogenicity that can be used to produce effective vaccines. The present disclosure further relates to a method for preventing viral infection, e.g., influenza virus infection.

2. Description of Related Art

Influenza virus infection has long been a serious epidemic disease among humans. Seasonal influenza viruses result in approximately 3 to 5 million severe infection cases and 290,000 to 650,000 deaths worldwide annually[1], while occasional emergence of human-infected avian influenza viruses (e.g., H5N1 and H7N9) further threatens human health and economics.

During influenza virus infection, the glycoprotein hemagglutinin (HA) is a key antigen determinant that is responsible for binding to host cell surface receptors (e.g., sialic acid-containing glycans) and subsequent endosomal membrane fusion. The HA protein of an influenza virus is comprised of HA1 and HA2 subunits, of which the HA1 subunit contains a receptor binding site (RBS) for binding to sialic acid receptors, whereas the HA2 subunit contains a fusion peptide and transmembrane domain (TM) that are responsible for trimerization [2]. Accordingly, the HA protein has become a primary target for developing anti-influenza drugs and vaccines.

However, researchers developing influenza vaccines readily encounter problems owing to the instability of the HA protein[3-6]. For instance, HA stability affects vaccine utility, as it significantly reflects vaccine immunogenicity and storage life[4, 7]. Unstable HAs may easily be subject to a post-fusion conformation or even dissociate into monomers that induces antibodies that recognize invalid epitopes, instead of the functionally neutralizing antibodies required to tackle infection, thereby resulting in not only reduced protection but also shortened vaccine shelf-life[3-6].

In 2013, the devastating H7N9 influenza virus was identified in China, which induced high mortality[9]. This virus has continued to circulate in China and has resulted in epidemics across the country. The H7N9 virus has been classified as a highly pathogenic avian influenza virus (HPAIV), so that effective vaccines for the H7N9 influenza virus are urgently needed for human and veterinary use[10]. However, the HA protein of the H7N9 influenza virus is relatively unstable that potentially reduces the efficacy of the respective vaccine for effective immunization. Therefore, there exists an unmet need for an effective vaccine that exhibits improved stability of the HA protein from an influenza virus without adversely impairing its immunogenicity.

SUMMARY

The present disclosure provides a chimeric HA protein that is a stabilizing chimeric antigen while maintaining proper immunogenicity, and thus is useful for producing an effective vaccine against an influenza virus. In the present disclosure, the HA1 subunit in the chimeric HA protein is a chimeric subunit, which means that the protein domains thereof are derived from different HA1 subunits, such as H7 and H3 subtypes.

In one embodiment of the present disclosure, the chimeric HA protein comprises an HA1 subunit and an HA2 subunit, wherein the HA1 subunit is composed of a first domain derived from a parental HA1 subunit of a first subtype influenza virus and a second domain derived from a parental HA1 subunit of a second subtype influenza virus. In another embodiment, the second domain in the HA1 subunit is at least one portion of an HA structural region selected from the group consisting of a fusion peptide pocket, an HA1 region near the spring-loaded long coiled-coil helix of the HA2 subunit, an HA1-HA1 interface, and an HA1-HA2 interface. In one embodiment, the HA2 subunit is an HA2 subunit of the first subtype influenza virus.

In one embodiment of the present disclosure, the first subtype influenza virus and the second subtype influenza virus are independently selected from the group consisting of H1 to H18 subtype influenza viruses, provided that the first subtype influenza virus and the second subtype influenza virus are different. In another embodiment, the first subtype influenza virus and the second subtype influenza virus are independently selected from the group consisting of H1, H2, H5, H6, H8, H9, H11 to H13, and H16 to H18 subtype influenza viruses, provided that the first subtype influenza virus and the second subtype influenza virus are different. In yet another embodiment, the first subtype influenza virus and the second subtype influenza virus are independently selected from the group consisting of H3, H4, H7, H10, H14, and H15 subtype influenza viruses, provided that the first subtype influenza virus and the second subtype influenza virus are different.

In one embodiment of the present disclosure, the first subtype influenza virus is an H7 subtype influenza virus, and the second subtype influenza virus is an H3 subtype influenza virus.

In one embodiment of the present disclosure, the parental HA1 subunit of the first subtype influenza virus is derived from an H7N9 influenza virus. In another embodiment, the parental HA1 subunit of the first subtype influenza virus has an amino acid sequence of SEQ ID NO: 1.

In one embodiment of the present disclosure, the parental HA1 subunit of the second subtype influenza virus is derived from an H3N2 influenza virus. In another embodiment, the parental HA1 subunit of the second subtype influenza virus has an amino acid sequence of SEQ ID NO: 2.

In one embodiment of the present disclosure, the HA1 subunit of the chimeric HA protein has an amino acid identity less than 100% as compared with the parental HA1 subunit of the first subtype influenza virus. In another embodiment, the HA1 subunit has an amino acid identity of at least 30% as compared with the parental HA1 subunit of the first subtype influenza virus. In yet another embodiment, the amino acid identity of the HA1 subunit to the parental HA1 subunit of the first subtype influenza virus is between 70% and 95%. In still another embodiment, the amino acid identity of the HA1 subunit to the parental HA1 subunit of the first subtype influenza virus is between 88% and 91%.

In one embodiment of the present disclosure, the chimeric HA protein comprises at least one of: (1) the fusion peptide pocket of the chimeric HA protein that includes Ala, Thr, Leu, Asn, Lys, and Arg; (2) the HA1 region near the spring-loaded long coiled-coil helix of the HA2 subunit of the chimeric HA protein that includes Asp and Ser; (3) the HA1-HA1 interface of the chimeric HA protein that includes Asn and Ser; and (4) the HA1-HA2 interface of the chimeric HA protein that includes Arg, Val, Lys, Ile, Tyr, and Ala.

In one embodiment of the present disclosure, the second domain in the HA1 subunit is derived from at least one amino acid, at least one peptide or a combination thereof selected from the group consisting of positions #11-#13, #21, #25, #27, #29, #31-#34, #37, #42, #44-#45, #46-#50, #53-#56, #58, #185-#189, #193, #216-#217, #219, #228, #268-#269, #271-#274, #276, #278-#280, #282-#285, #287, #289-#292, #297-#302, #304, #307, #312-#313, #315, #321, and #326-#329 of SEQ ID NO: 2; for example, positions #11-#13 refer to a peptide with three consecutive amino acids at positions 11 to 13 of SEQ ID NO: 2, and #21 refers to a single amino acid at position 21 of SEQ ID NO: 2.

In one embodiment of the present disclosure, the chimeric HA protein comprises at least one of: (1) the fusion peptide pocket including Ala, Thr, Leu, Asn, Thr, Lys, and Arg at positions 1, 2, 3, 303, 304, 306, and 312 in SEQ ID NO: 12, respectively; (2) the HA1 region near the spring-loaded long coiled-coil helix of the HA2 subunit, the HA1 region including Asp and Ser at positions 22 and 35 in SEQ ID NO: 12, respectively; and (3) the HA1-HA1 interface including Asn and Ser at positions 207 and 210 in SEQ ID NO: 12, respectively.

In one embodiment of the present disclosure, the chimeric HA protein comprises the HA1-HA2 interface including Arg, Val, Lys, Ile, Tyr, Ala, and Lys at positions 259, 287, 289, 290, 292, 294, and 297 in SEQ ID NO: 13, respectively.

In one embodiment of the present disclosure, the HA1 subunit of the chimeric HA protein comprises an amino acid sequence selected from the group consisting of SEQ ID NOs: 3 to 8.

In one embodiment of the present disclosure, a vaccine composition is provided. The vaccine composition comprises the chimeric HA protein of the present disclosure and a pharmaceutically acceptable carrier and/or an adjuvant. In another embodiment, the adjuvant is at least one of a squalene adjuvant, a cytokine adjuvant, a lipid adjuvant and a Toll-like receptor (TLR) ligand.

In one embodiment of the present disclosure, the chimeric HA protein in the vaccine composition is present in an effective amount to prevent influenza virus infection, or to induce an immune response against an influenza virus in a subject in need thereof.

In one embodiment of the present disclosure, the vaccine composition is suitable for administration via intranasal, intramuscular, intravenous, intra-arterial, intraperitoneal, intrathecal, intraventricular, subcutaneous and mucosal routes.

In one embodiment of the present disclosure, a method is provided for inducing an immune response against an influenza virus in a subject in need thereof. In one embodiment, the method is provided for conferring protection against influenza virus infection on the subject. In one embodiment of the present disclosure, the influenza virus is an H1N1, H1N2, H2N2, H3N2, H5N1, H5N2, H5N6, H6N1, H7N2, H7N3, H7N7, H7N9, H9N2, H10N7 or H10N8 influenza virus. In another embodiment, the influenza virus is an H7N9 influenza virus.

In one embodiment of the present disclosure, the method comprises administering the vaccine composition of the present disclosure to the subject. In another embodiment, the subject is a vertebrate. In still another embodiment, the subject is a mammal, such as a human.

In the present disclosure, the chimeric HA proteins provided by the present disclosure not only achieve the construction of a more stable HA antigen, but also facilitate effective vaccine improvements to fight against infection of influenza viruses.

BRIEF DESCRIPTION OF THE DRAWINGS

The present disclosure can be more fully understood by reading the following descriptions of the embodiments, with reference made to the accompanying drawings.

FIG. 1A shows the non-identical amino acids between the H7-HA1 and H3-HA1 subunits divided by SCHEMA into six blocks according to their known protein structures and sequence alignment. FIG. 1B depicts the six blocks shown in the H7-HA1 structure. The division of these six blocks are consistent across individual domains of the 3D structure, except for the block B that is divided into two sub-domains which are non-continuous across the peptide sequence. H7-HA1 represents the HA1 subunit from the H7 protein (i.e., the HA protein from an H7 subtype influenza virus), and H3-HA1 represents the HA1 subunit from the H3 protein (i.e., the HA protein from an H3 subtype influenza virus).

FIG. 3A shows the constructs of expression vectors of the full-length parental and chimeric HAs. All constructs are driven by the polyhedrin promoter (p-polh), fused with an N-terminal GP64 signal peptide (SP) and a hexameric histidine tag (6H), and include a pag promoter (p-pag) driving the DsRed gene as a reporter. The six chimeric HA proteins, FrA to FrF, were constructed by fusing the HA2 subunit from the H7 subtype influenza virus to the C-termini of individual rA to rF chimeric HA1 subunits. WT-DR virus was generated by an empty vector containing only the DsRed reporter as a negative control. FIG. 3B shows the Western blot analysis of the full-length HA constructs. Insect cells were infected by recombinant baculoviruses expressing each of the HA constructs at a multiplicity of infection (MOI) equal to 1. Cell lysates were harvested at 2 days post infection (d.p.i.) before performing Western blot by using the anti-His antibody. Glyceraldehyde 3-phosphate dehydrogenase (GAPDH) was detected by the anti-GAPDH antibody as a loading control.

FIG. 4A shows the fusion peptide pocket of the chimeric HA protein FrB, wherein Ala 1, Thr 2, Leu 3, Asn 303, Thr 304, Lys 306, and Arg 312 refer to the amino acids and their positions of the chimeric rB-HA1 subunit (SEQ ID NO: 12). FIG. 4B shows the HA1 region near the spring-loaded long coiled-coil helix of the HA2 subunit of the chimeric HA protein FrB, wherein Asp 22 and Ser 35 refer to the amino acids and their positions of the chimeric rB-HA1 subunit (SEQ ID NO: 12). FIG. 4C shows the HA1-HA1 interface of the chimeric HA protein FrB, wherein Asn 207 and Ser 210 refer to the amino acids and their positions of the chimeric rB-HA1 subunit (SEQ ID NO: 12). FIG. 4D shows the HA1-HA2 interface of the chimeric HA protein FrC, wherein Arg 259, Val 287, Lys 289, Ile 290, Tyr 292, Ala 294, and Lys 297 refer to the amino acids and their positions of the chimeric rC-HA1 subunit (SEQ ID NO: 13). The HA1-HA2 interface shown in FIG. 4D is present by two diagrams, in order to clearly illustrate the multiple amino acids.

FIG. 8A illustrates the schematic hemagglutination assay, wherein in the absence of HA-expressing samples, red blood cells precipitate in the V-bottom wells that forms a dot at the center of each well; upon encountering HA-expressing samples, the red blood cells clump with HA-displaying insect cells to form lattices and produce a diffuse pale red signal in V-bottom wells. FIG. 8B shows the hemagglutination assay of the recombinant baculovirus-infected Sf21 cells, wherein the HA titer of each sample was determined as the reciprocal of the highest dilution with remaining HA activity. Phosphate-buffered saline (PBS) refers to the buffer-only control; HA: purified H7 protein (representing 500 ng in the first row); Non: non-infected Sf21 cells.

FIG. 10A shows sera (1:10,000) from mice (n=5) immunized intraperitoneally with purified FH7, FrB, or FrC proteins or PBS and then collected at week 6 and week 8 after primary immunization, before measuring the specific anti-HA IgG antibody binding levels by indirect ELISA against purified FH7 protein. Data are expressed as mean values±SD for five mice in each group with technical triplicates. FIG. 10B shows the microneutralization assay of FH7-, FrB- or FrC-immunized mouse sera against an H7N9 influenza virus (the A/Taiwan/01/2013 strain) infection. The mouse sera were serially diluted 2-fold (initial concentration 1:10), and mixed with 10 times the 50% tissue culture infective doses ($TCID_{50}$) of the H7N9 influenza virus to determine microneutralization titers (the reciprocal of the highest dilution without CPE) in the infected MDCK cells. Data are expressed as mean values±SD for five mice in each group with technical quadruplicates. * refers to significant difference ($p<0.05$) versus PBS; † refers to significant difference ($p<0.05$) versus FH7 at designated time points.

DETAILED DESCRIPTION OF THE EMBODIMENTS

Figure 1A:
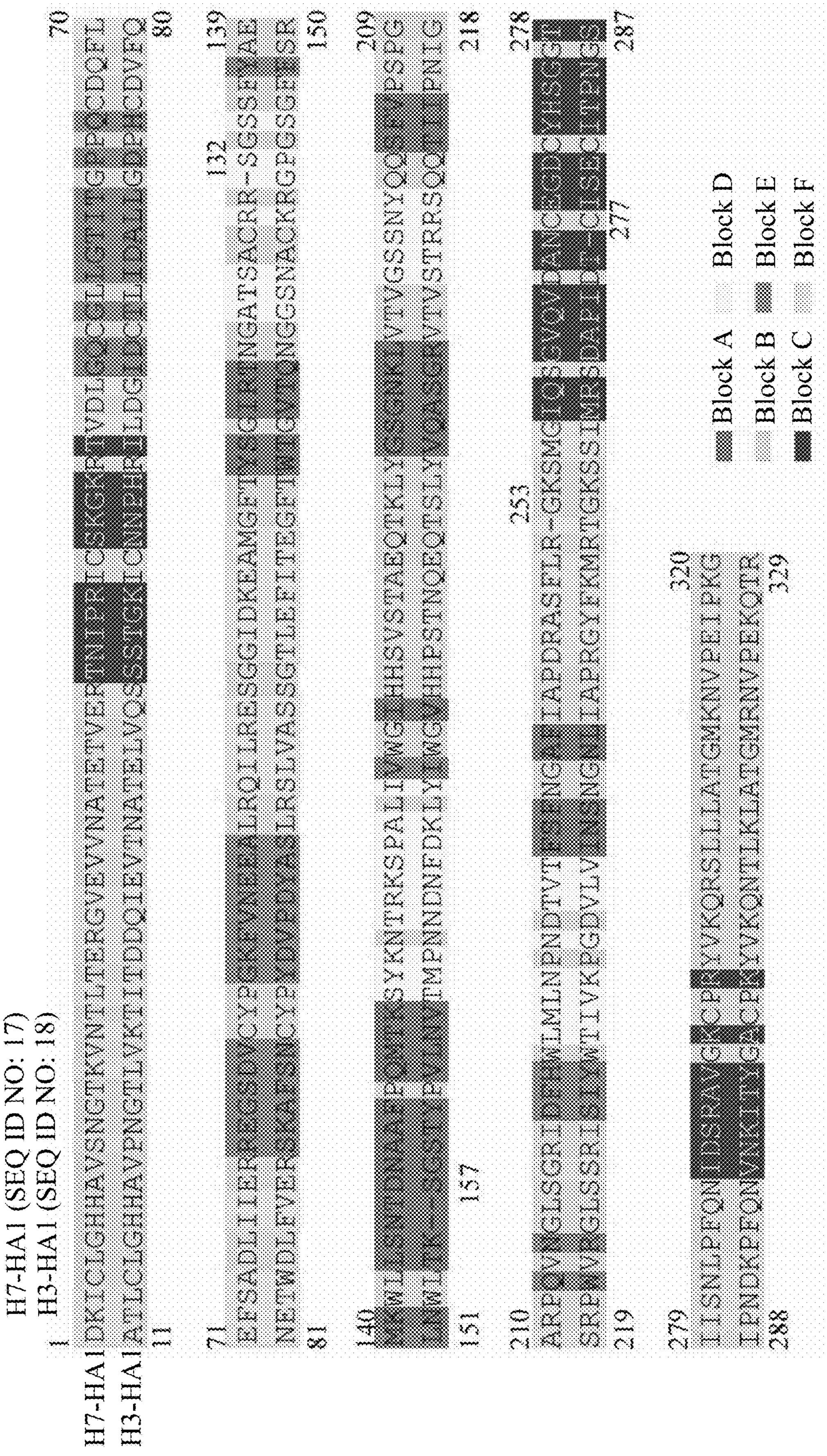
FIGS. 1A and 1B illustrate the non-contiguous SCHEMA recombination of H7-HA1 and H3-HA1.

The following examples are used for illustrating the present disclosure. A person skilled in the art can easily conceive the other advantages and effects of the present disclosure, based on the disclosure of the specification. The present disclosure can also be implemented or applied as described in different examples. It is possible to modify or alter the following examples for carrying out this disclosure without contravening its spirit and scope, for different aspects and applications.

It is further noted that, as used in this disclosure, the singular forms "a," "an," and "the" include plural referents unless expressly and unequivocally limited to one referent. The term "or" is used interchangeably with the term "and/or" unless the context clearly indicates otherwise.

The present disclosure is directed to chimeric HA proteins and their uses as stable HA antigens in a vaccine composition for prevention of viral infections.

The chimeric HA protein of the present disclosure comprises a chimeric HA1 subunit, which comprises a first domain derived from a parental HA1 subunit of a first subtype influenza virus and a second domain derived from a parental HA1 subunit of a second subtype influenza virus.

In one embodiment of the present disclosure, the first subtype influenza virus and the second subtype influenza virus are independently selected from the group consisting of H1 to H18 subtype influenza viruses, provided that the first subtype influenza virus and the second subtype influenza virus are different. In another embodiment of the present disclosure, the first subtype influenza virus and the second subtype influenza virus are independently selected from Group I influenza viruses, such as H1, H2, H5, H6, H8, H9, H11 to H13, and H16 to H18 subtype influenza viruses, or Group II influenza viruses, such as H3, H4, H7, H10, H14, and H15 subtype influenza viruses.

The term "chimeric HA protein," "chimeric protein," or "chimeric subunit" as used herein refers to a single polypeptide unit that comprises at least two heterological domains joined by a peptide bond(s), wherein the different domains are not naturally occurring within the same polypeptide unit. As to the amino acid sequence of the chimeric protein, each heterological domain may correspond to non-continuous amino acids or a number of peptide fragments. These non-continuous amino acids and peptide fragments may assemble as an integrated and structurally interacting domain. For instance, such chimeric proteins may be obtained by expression of a cDNA construct or by protein synthesis methods known in the art.

For example, the chimeric HA1 subunits of the present disclosure may contain two domains derived from the HA protein subtypes H7 and H3 (i.e., the HA proteins from the H7 subtype influenza virus and the H3 subtype influenza virus, respectively), which means that such chimeric subunits may contain a plurality of non-continuous amino acids and/or a plurality of peptide fragments homological to a naturally occurring HA1 subunit of the HA protein from the H7 subtype influenza virus, and a plurality of non-continuous amino acids and/or a plurality of peptide fragments homological to a naturally occurring HA1 subunit of the HA protein subtype H3.

The term "domain" or "protein block" as used herein refers to a set of at least one amino acid, at least one peptide, or a combination thereof in a protein. That is to say, a domain of a protein may include only one amino acid, a plurality of non-continuous amino acids, only one peptide, a plurality of peptide, or a combination thereof. For example, the first domain in the chimeric HA1 subunit of the present disclosure may be composed of amino acid(s) which is/are derived from the parental HA1 subunit of the first subtype influenza virus. In addition, some of the amino acid(s) in the domain of the protein may constitute a portion of a structural region of the protein.

In one embodiment of the present disclosure, the HA1 subunit of the chimeric HA protein is derived from the parental HA1 subunits, e.g., the naturally occurring HA1 subunits of the H7N9 influenza virus and the H3N2 influenza virus. In another embodiment, the H7N9 influenza virus is an A/Anhui/1/2013 strain, and the H3N2 influenza virus is an A/Hong Kong/1/1968 strain.

In one embodiment of the present disclosure, the parental HA1 subunit of the first subtype influenza virus includes an amino acid sequence at least 70%, 75%, 80%, 85%, 88%, 90%, 92%, 95%, 96%, 97%, 98%, or 99% identical to the amino acid sequence of SEQ ID NO: 1. In another embodiment, the parental HA1 subunit of the first subtype influenza virus has the amino acid sequence of SEQ ID NO: 1.

In one embodiment of the present disclosure, the parental HA1 subunit of the second subtype influenza virus includes an amino acid sequence at least 70%, 75%, 80%, 85%, 88%, 90%, 92%, 95%, 96%, 97%, 98%, or 99% identical to the amino acid sequence of SEQ ID NO: 2. In another embodiment, the parental HA1 subunit of the second subtype influenza virus has the amino acid sequence of SEQ ID NO: 2.

In one embodiment of the present disclosure, the amino acid identity of the HA1 subunit of the chimeric HA protein as compared with the parental HA1 subunit of the first subtype influenza virus is from 30% to less than 100%, and the chimeric HA protein containing such HA1 subunit has higher thermal stability and comparable immunogenicity in comparison with the HA protein containing the parental HA1 subunit. In one embodiment, the HA1 subunit of the chimeric HA protein has less than 95% amino acid identity as compared with the parental HA1 subunit of the first subtype influenza virus. In another embodiment, the HA1 subunit of the chimeric HA protein has at least 70% amino acid identity as compared with the parental HA1 subunit of the first subtype influenza virus. In yet another embodiment, the amino acid identity of the HA1 subunit of the chimeric HA protein as compared with the parental HA1 subunit of the first subtype influenza virus is between 71% and 94%, such as 75%, 80%, 85%, 88%, 89%, 90%, 91%, 92%, 93% and 94%.

In one embodiment of the present disclosure, the HA1 subunit of the chimeric HA protein includes an amino acid sequence at least 70%, 75%, 80%, 85%, 88%, 90%, 92%, 95%, 96%, 97%, 98%, or 99% identical to the amino acid sequence selected from the group consisting of SEQ ID NOs: 3 to 8, and has the same functions as SEQ ID NOs: 3 to 8, respectively. In another embodiment, the HA1 subunit of the chimeric HA protein has an amino acid sequence selected from the group consisting of SEQ ID NOs: 3 to 8.

In one embodiment of the present disclosure, the chimeric HA protein includes an amino acid sequence at least 70%, 75%, 80%, 85%, 88%, 90%, 92%, 95%, 96%, 97%, 98%, or 99% identical to the amino acid sequence selected from the group consisting of SEQ ID NOs: 11 to 16, and has the same functions as SEQ ID NOs: 11 to 16, respectively. In another embodiment, the chimeric HA protein has an amino acid sequence selected from the group consisting of SEQ ID NOs: 11 to 16.

In one embodiment of the present disclosure, the second domain in the chimeric HA1 subunit is at least one portion of an HA structural region selected from the group consisting of a fusion peptide pocket, an HA1 region near the spring-loaded long coiled-coil helix of the HA2 subunit, an HA1-HA1 interface, and an HA1-HA2 interface.

For example, the HA structural regions may include: (1) a fusion peptide pocket, i.e., a region near the "F domain" of the HA1 subunit which surrounds the fusion peptide; (2) an HA1 region near the spring-loaded long coiled-coil helix of the HA2 subunit; (3) an HA1-HA2 interface, i.e., a region of the interface between the HA1 receptor-binding domain protomers; or (4) an HA1-HA1 interface, i.e., a region between the receptor-binding domain, esterase subdomain, helix C, and loop B.

In one embodiment of the present disclosure, the chimeric HA protein may comprise at least one of: (1) the fusion peptide pocket of the chimeric HA protein that includes Ala, Thr, Leu, Asn, Lys, and Arg; (2) the HA1 region near the spring-loaded long coiled-coil helix of the HA2 subunit of the chimeric HA protein that includes Asp and Ser; (3) the HA1-HA1 interface of the chimeric HA protein that includes Asn and Ser; and (4) the HA1-HA2 interface of the chimeric HA protein that includes Arg, Val, Lys, Ile, Tyr, and Ala.

In one embodiment of the present disclosure, a portion of the amino acid residue(s) in the chimeric HA1 subunit is replaced by the amino acid residue(s) at corresponding position(s) of the parental HA1 subunit of the second subtype influenza virus, so as to form the second domain in the chimeric HA1 subunit. In another embodiment, the second domain is derived from at least one amino acid, at least one peptide or a combination thereof selected from the group consisting of positions #11-#13, #21, #25, #27, #29, #31-#34, #37, #42, #44-#45, #46-#50, #53-#56, #58, #185-#189, #193, #216-#217, #219, #228, #268-#269, #271-#274, #276, #278-#280, #282-#285, #287, #289-#292, #297-#302, #304, #307, #312-#313, #315, #321, and #326-#329 of SEQ ID NO: 2.

The term "sequence identity," "amino acid identity," or "homology" as used herein refers to describe sequence relationships between two or more nucleotide sequences or amino acid sequences. The percentage of the "sequence identity" between two sequences is determined by comparing two optimally aligned sequences over a comparison window, wherein the portion of the sequence in the comparison window may comprise additions or deletions (e.g., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. Included are nucleotides or polypeptides having at least about 70%, 75%, 80%, 85%, 88%, 90%, 92%, 95%, 97%, 98%, 99% or 100% sequence identity to any of the reference sequences described herein (see, e.g., Sequence Listing), where the polypeptide variant maintains at least one biological activity or function of the reference polypeptide.

In certain embodiments of the present disclosure, vaccine compositions are provided for primary immunization of a subject against influenza. In the present disclosure, the vaccine composition may include a chimeric HA protein of the present disclosure as a main antigen for use in the reduction of severity or for use in the prevention of influenza infections. In other embodiments, methods for reducing the severity or preventing influenza infections by using the vaccine composition of the present disclosure are also provided.

In one embodiment of the present disclosure, the chimeric HA protein in the vaccine composition is present in an effective amount to prevent influenza virus infection, or to induce an immune response against an influenza virus in a subject in need thereof. In another embodiment, the vaccine composition is administered in an amount sufficient to elicit an immune response against an influenza virus, such as the H7N9 subtype, in a subject in need thereof.

In one embodiment of the present disclosure, the vaccine composition may further comprise a pharmaceutically acceptable carrier and/or an adjuvant. In another embodiment, the adjuvant is at least one of a squalene adjuvant, a cytokine adjuvant, a lipid adjuvant and a Toll-like receptor (TLR) ligand. The examples of the TLR ligand includes, but are not limited to, 3-deacylated monophoshoryl lipid A (3D-MPL), lipopolysaccharide (LPS), muramyl dipeptide (MDP), and CpG motifs. In yet another embodiment, the vaccine composition administered to the subject comprises a mixture of the chimeric HA protein as an antigen and the adjuvant at a weight ratio of 10:1 to 1:10.

The term "pharmaceutically acceptable carrier" as used herein refers to any and all solvents, dispersion media, antibacterial and antifungal agents, isotonic and absorption delaying agents and the like which may be appropriate for administration of the vaccine composition of the present disclosure. The pharmaceutically acceptable carrier useful for the present disclosure may include, but not be limited to, a preservative, a suspending agent, a tackifier, an isotonicity agent, a buffering agent, a humectant, and a combination thereof.

In one embodiment of the present disclosure, the vaccine composition may be administered by any suitable delivery route, such as intranasal, intramuscular, intravenous, intra-arterial, intraperitoneal, intra-thecal, intraventricular, subcutaneous and mucosal routes. In another embodiment, the vaccine composition of the present disclosure is administered to a subject under conditions sufficient to prevent influenza infection in the subject.

In one embodiment of the present disclosure, a method is provided for inducing an immune response against an influenza virus in a subject in need thereof. In another embodiment, the influenza virus is H1N1, H1N2, H2N2, H3N2, H5N1, H5N2, H5N6, H6N1, H7N2, H7N3, H7N7, H7N9, H9N2, H10N7 or H10N8 subtype influenza virus. In yet another embodiment, the subject is a vertebrate. In still another embodiment, the subject is a mammal, such as a human.

In one embodiment of the present disclosure, the method comprises administering a vaccine composition comprising a chimeric HA protein to a subject in need thereof, wherein the chimeric HA protein comprises an HA1 subunit composed of a first domain and a second domain, and wherein the first domain is derived from a parental HA1 subunit of a first subtype influenza virus, and the second domain is derived from a parental HA1 subunit of a second subtype influenza virus. In another embodiment, the parental HA1 subunit of the first subtype influenza virus is derived from an H7N9 subtype influenza virus, such as an A/Anhui/1/2013 strain, and may have the amino acid sequence of SEQ ID NO: 1. In yet another embodiment, the parental HA1 subunit from the HA protein of the second subtype influenza virus is derived from an H3N2 influenza virus, such as an A/Hong Kong/1/1968 strain, and may have the amino acid sequence of SEQ ID NO: 2.

In one embodiment of the present disclosure, the amino acid identity of the HA1 subunit of the chimeric HA protein as compared with the parental HA1 subunit from the HA protein of the first subtype influenza virus is between 70% and 95%. In another embodiment, the HA1 subunit of the chimeric HA protein comprises an amino acid sequence selected from the group consisting of SEQ ID NOs: 3 to 8.

In one embodiment of the present disclosure, the chimeric HA protein further comprises an HA2 subunit that may be an HA2 subunit from the first subtype influenza virus, such as an H7N9 subtype influenza virus.

In an embodiment of the present disclosure, the chimeric HA protein has improved stability and enhanced immunogenicity in comparison with the naturally occurring HA protein of the influenza virus, such as the H7N9 subtype influenza virus, such that the chimeric HA protein of the present disclosure may be used as a better vaccine antigen.

Many examples have been used to illustrate the present disclosure. The examples below should not be taken as a limit to the scope of the present disclosure.

EXAMPLES

Materials and Methods

The materials and methods used in the following Examples 1-5 were described in detail below. The materials used in the present disclosure but unannotated herein are commercially available.

(1) Non-Contiguous SCHEMA Recombination

The amino acid sequences of H7-HA1 (i.e., the HA1 subunit from the H7 protein) and H3-HA1 (i.e., the HA1 subunit from the H3 protein) were aligned by ROMALS3D [17]. The resulting alignment and protein structures of H7-HA1 and H3-HA1 were used as input for non-contiguous SCHEMA recombination to create SCHEMA contact maps, in which the SCHEMA algorithm considered any two amino acids as being in contact if any atoms (excluding hydrogen) from the two amino acids were within 4.5 Å of each other. The structure of H7-HA1 was derived from Protein Data Bank (PDB) Accession No. 4LN6[18] chain A. For H3-HA1, it was PDB Accession No. 4WE4[19] chain A. SCHEMA distributed the non-identical residues of these two HA1s into blocks and calculated the number of disrupted contacts upon block swapping for each chimera (represented as the E value) relative to the closest parental protein.

(2) Viral DNA and Plasmid DNA

The cDNA sequences of the full-length A/Anhui/1/2013 (H7N9) and A/Hong Kong/1/1968 (H3N2) HA, as well as of the six chimeric HA1s, were synthesized by GenScript, U.S.A. The FH7 and FH3 coding regions including the ectodomain, transmembrane domain, and cytoplasmic tail domain were amplified from the A/Anhui/1/2013 (H7N9) and A/Hong Kong/1/1968 (H3N2) HA cDNAs, respectively, and then inserted along with the AcMNPV GP64 signal peptide and a hexametric histidine tag at the N-terminal into a baculovirus transfer vector, pBacPAK8 (Clontech). The DsRed gene driven by the pag promoter[11, 12] was also inserted into the vector to serve as the reporter gene. Sequences of chimeric HA1 proteins were individually cloned into the transfer vector of FH7 to replace the HA1 portion. The empty vector pBacPAK8 with only the pag-dsRed reporter gene was used as the transfer vector for the WT-DR virus.

(3) Cells and Viruses

*Spodoptera frugiperda* IPLB-Sf21 (Sf21) cells were cultured at 26° C. in TC100 insect medium (Gibco, Thermo Fisher Scientific) with 10% fetal bovine serum (FBS). Recombinant AcMNPVs were generated by co-transfecting the transfer vector plasmids carrying HA constructs with FlashBAC (Mirus, a modified AcMNPV baculovirus genome) into Sf21 cells by Cellfectin (Life Technologies). The resulting recombinant baculoviruses were propagated in Sf21 and isolated through end-point dilutions as previously described[20, 21]. *Trichoplusia ni* BTI-TN-5B1-4 (Hi5) cells were cultured at 26° C. in ESF serum-free insect cell culture medium (Expression Systems) without adding FBS. Madin-Daby canine kidney (MDCK) cells were cultured in a monolayer at 37° C. and 5% $CO_2$ using Dulbecco's Modified Eagle's medium (DMEM) (Sigma, St. Louis, MO) supplemented with 10% FBS.

(4) Recombinant HA Protein Expression and Western Blotting Analysis

Sf21 cells were infected by recombinant viruses at MOI equal to 1 and incubated for 2 days to express the recombinant proteins. The cells were collected, washed with Dulbecco's phosphate-buffered saline (DPBS) to remove the culture medium, and lysed by RIPA Lysis and Extraction Buffer (Thermo Scientific). Equal amounts of cell lysates were separated by 10% sodium dodecyl sulfate-polyacrylamide gel (Omic Bio) and Western blotted using mouse anti-His antibody (1:5,000, GeneTex GTX628914) to determine protein expression. Expression of GAPDH for each sample was determined using rabbit anti-GAPDH (10,000, GeneTex GTX100118) as a loading control.

(5) Immunofluorescence Assay to Detect the Expression of HA

Sf21 cells ($1\times10^4$) were seeded into 8-well Millicell EZ slides (Millipore), and the cells were infected with recombinant baculovirus using MOI equal to 1, before fixing cells with 4% paraformaldehyde at 2 d.p.i. For cells requiring additional permeabilization, 0.2% Triton (prepared in DPBS) was added into the cells, and then the cells were incubated for 5 min. After blocking with 3% bovine serum albumin (BSA) in DPBS for 1 h, the cells were incubated with mouse anti-His-tagged antibody (1:5000, GeneTex GTX628914) overnight at 4° C. The cells were washed three times with DPBST (DPBS, plus 0.1% Tween 20) and incubated with 1:200-diluted Alexa Fluor goat anti-mouse IgG secondary antibody (Invitrogen). Images were obtained with a Zeiss laser confocal microscope (LSM780) and analyzed by ZEN 2010 software (Zeiss).

(6) Cell-Based Enzyme-Linked Immunosorbent Assay (ELISA)

Sf21 cells were cultured in a 96-well plate and infected with recombinant baculoviruses using MOI equal to 1 to display HA protein antigens on cell surfaces. Culture medium was removed at 3 d.p.i., and the cells were washed by DPBS. The cells were then fixed by 4% paraformaldehyde and permeabilized by 0.2% Triton treatment. The permeabilized cells were incubated with the blocking buffer (3% BSA in DPBS) for 1 h at room temperature. The H7N9 H7-specific neutralizing monoclonal antibody (11082-R002, Sino Biological Inc.) was diluted 1:5,000 in the blocking buffer, added to the cell samples, and then incubated overnight at 4° C. After three washes with 0.1% Tween 20 in PBS (PBST), horseradish peroxidase (HRP)-conjugated goat anti-rabbit IgG antibody (diluted 1:10,000; Merck Millipore) was added to each well for 1 h at room temperate. The samples were washed three times with PBST and the 3,3',5,5'-tetramethyl benzidine (TMB) substrate was then added. Coloring reactions were stopped using 2 M sulfuric acid, and ELISA absorbance was measured at 450 nm. The average read of cell served only as a blank for other samples.

(7) Hemagglutination Assay

To ensure higher recombinant protein expression, Hi5 cells were used in the hemagglutination assay. Optimal hemagglutination activity of cell surface-expressed HAs was determined at 5 d.p.i. of recombinant viruses at MOI equal to 0.5. The infected Hi5 cells were collected from the monolayer cultures, and centrifuged to remove the culture medium. The pelleted cells were suspended in PBS (pH 7.2) plus 0.01% BSA and disrupted by a brief sonication. Fifty microliters of the disrupted cell suspension was added into the V-bottom 96-well plates and serially diluted 2-fold to a final 256-fold dilution. Fifty microliters of 1% turkey erythrocytes (suspended in PBS containing 0.01% BSA) were added into each well and incubated for 1 h at room temperature. The hemagglutination titer was defined as the reciprocal of the highest dilution to agglutinate turkey erythrocytes.

(8) Thermal Stability Assay Measured by Loss of Hemagglutination Titer

The infected Hi5 cell samples exhibiting HA expression were prepared to HA titers of 64 per 50 μL and incubated at 50° C. for 0, 5, 10, 20, 30, 60, 90, and 120 min. After being cooled down to 4° C., the samples were subjected to the hemagglutination assay to determine the loss of hemagglutination titer.

(9) Protein Purification for Mice Immunizations

To purify the HA proteins for mice immunization, Hi5 cells were infected by vFH7, vFrB, and vFrC, respectively, at MOI equal to 5. The cells were harvested at 4 d.p.i. by low-speed centrifugation. Cell pellets were treated with I-PER Insect Cell Protein Extraction Reagent (Thermo Scientific) (with the addition of 1% Triton) on ice for 10 min to extract the recombinant HAs. Cell lysates were clarified by centrifugation at 10,000×g for 30 min, and the supernatants were loaded on metal affinity chromatography columns packed with Ni Sepharose 6 Fast Flow resin (GE Healthcare). The columns were washed with carbonate wash buffer (50 mM $NaHCO_3$, 300 mM NaCl, 20 mM imidazole, pH 8), and recombinant HAs were eluted with an elution buffer (50 mM $NaHCO_3$, 300 mM NaCl, 300 mM imidazole, pH 8). The purified proteins were dialyzed in the PBS buffer and then concentrated by Amicon Ultra Centrifugal Filter Units (Merck Millipore). Protein concentrations were determined by using a Coomassie Plus (Bradford) Assay Kit (Thermo Scientific).

(10) Mice Immunizations

All mice for immunization assays were purchased from the Taiwan National Laboratory Animal Center, and the experimental procedures were approved by the Institutional Animal Care and Use Committee (IACUC) of Academia Sinica, Taiwan. Five female BALB/c mice (6- to 8-weeks-old) per group were immunized intraperitoneally with 30 μg of each purified full-length recombinant protein homogenized with Freund's complete adjuvant. The negative control group was immunized with PBS only. Two boost shots, each of 30 μg antigen in Freund's incomplete adjuvant, were administered 2 and 4 weeks after the primary immunization. Serum was collected from all mice at 6 and 8 weeks after the primary immunization.

(11) Indirect ELISA Assay to Measure Serum H7-Specific IgG

Levels of serum IgG-specific antibodies against FH7 antigen were determined for each serum sample by indirect ELISA according to a previously described method[22]. Purified FH7 (20 ng/well) was coated on the 96-well plate overnight at 4° C. After blocking by 3% BSA (in DPBS) for 1 h, mouse sera (1:10,000 dilution) were added to the wells in triplicate and incubated for 2 h at room temperature. The wells were then washed three times with DPBST, before adding goat anti-mouse IgG conjugated with HRP (Merck Millipore) and incubating for 1 h. After three washes by PBST, the TMB substrate was added to each well. The coloring reactions were stopped using 2 M sulfuric acid, and ELISA absorbance was measured at 450 nm using an ELISA plate reader.

(12) Serum Microneutralization Assay

The A/Taiwan/01/2013 (H7N9) influenza virus was first amplified, and its $TCID_{50}$ was determined in MDCK cells. Collected mouse sera were filtered using a 0.22 μm filter, serially diluted 2-fold (from 1:10 to 1:1,280), mixed with 10 $TCID_{50}$ of H7N9 virus, and incubated at 4° C. for 1 h. The mixtures were then transferred to monolayer MDCK cells in 96-well plates and cultured at 37° C. Neutralizing activity was determined at 3 d.p.i. by observing the virus-induced cytopathic effect (CPE), and the microneutralizing titer was defined as the reciprocal of the highest dilution that totally prevented the CPE. For statistical analysis, each serum sample was assessed in quadruplicate.

(13) Statistical Analyses

For cell-based ELISA, thermal hemagglutination assays, indirect ELISA, and serum microneutralization assay, each condition was analyzed with at least three replicates (or quadruplicate for the microneutralization assay). All quantitative data are shown as means±SD (error bars). Statistical analysis was performed using unpaired t-test (Excel 2016 software; Microsoft) for two group comparisons, and P-values<0.05 were considered significant.

Example 1: Construction of the Chimeric HA1 Subunit

For improving stability of the H7 protein (i.e., the HA protein from an A/Anhui/1/2013 strain (the H7N9 subtype)), the H3 protein from an A/Hong Kong/1/1968 strain (the H3N2 subtype) was selected for recombination with the H7 protein, because both the two subtypes belong to group II influenza viruses and the H3 protein (i.e., the HA protein from the H3 subtype influenza virus) is phylogenetically related to the H7 protein (i.e., the HA protein from the H7 subtype influenza virus).

SCHEMA, which is a computational algorithm used in protein engineering to identify fragments of proteins (called as protein blocks or domains) that can be recombined without disturbing the integrity of the three-dimensional structure of the protein in interest, was employed in this Example for construction of the chimeric protein.

The selected H7 and H3 proteins exhibit 49% identity to each other. For instance, the HA1 subunits present 38% identity, whereas the HA2 subunits have 68% identity. Since the HA1 subunit of the HA protein is primarily responsible for sequence divergence and harbors most of the antigenic sites, the HA1 subunit of the H7 protein (H7-HA1; SEQ ID NO: 1) and the HA1 subunit of the H3 protein (H3-HA1; SEQ ID NO: 2) were collected for providing a total of non-identical amino acids for block assignment. The SCHEMA algorithm distributed these non-identical residues into different blocks according to structural adjacency and calculated E values representing the number of residue-residue contacts (two amino acids with at least one non-hydrogen atom within 4.5 Å) that would be broken in a chimera upon block swapping between two proteins.

Figure 1B:
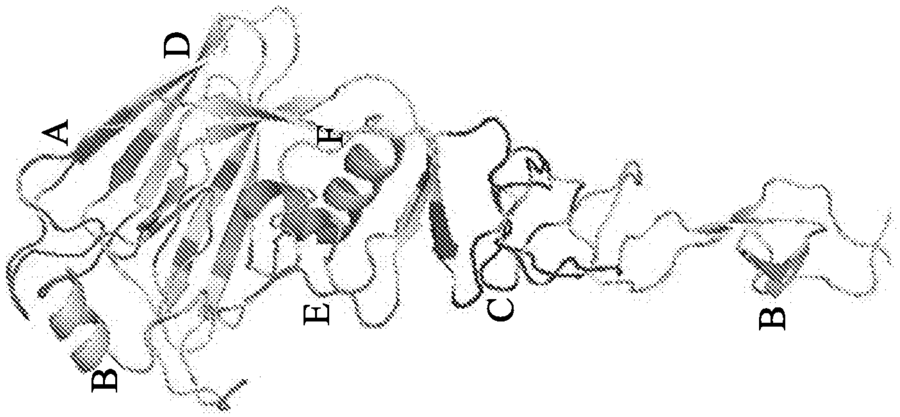

It was decided to divide the HA1 subunits of the H7 and H3 proteins into six blocks (block A to block F), which nearly distribute the 201 non-identical amino acids of the two HA1 subunits evenly. These divisions are non-continuous along the peptide sequence (FIG. 1A), but the amino acids in each block are assembled as an integrated and structurally interacting domain (FIG. 1B). The only exception is block B, which SCHEMA further divided it into two sub-blocks; one representing the N and C termini joined together as a sub-block (the lower portion shown in FIG. 1B), and the other comprising the remaining amino acids in the HA head domain (the upper portion shown in FIG. 1B).

Figure 2:
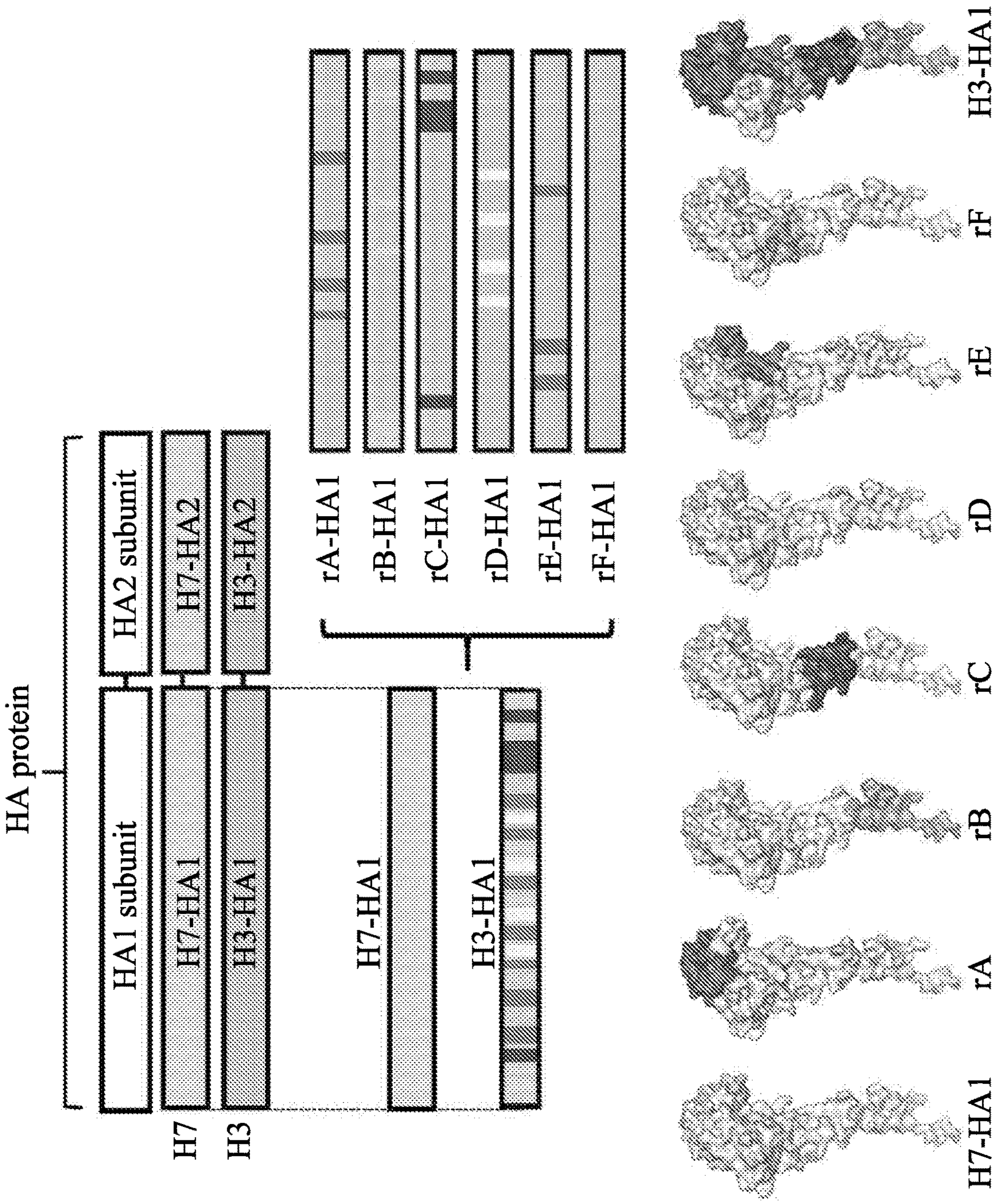
FIG. 2 illustrates different constructs of the HA1 subunits and their 3D structures, wherein H7-HA1 refers to the HA1 subunit from the H7 subtype influenza virus; H3-HA1 refers to the HA1 subunit from the H3 subtype influenza virus; H7-HA2 refers to the HA2 subunit from the H7 subtype influenza virus; H3-HA2 refers to the HA2 subunit from the H3 subtype influenza virus; and rA-HA1 to rF-HA1 refer to the six chimeric HA1 subunits.

Each of the chimeric proteins was designed to solely have one block swapped from the H3 protein and the rest of the protein originated from the H7 protein, which resulted in six individual clones (designated as rA to rF, Table 1 and FIG. 2). The amino acid sequences of the chimeric HA1 subunits rA to rF are represented by SEQ ID NOs: 3 to 8, respectively.

TABLE 1

Parental and SCHEMA-derived chimeric HA1 subunits

| | | Inherited block | | | | | | | |
|---|---|---|---|---|---|---|---|---|---|
| Protein | | A | B | C | D | E | F | E | m |
| Parental | H7 | 7 | 7 | 7 | 7 | 7 | 7 | 0 | 0 |
| | H3 | 3 | 3 | 3 | 3 | 3 | 3 | 0 | 0 |
| Selected chimeras | rA | 3 | 7 | 7 | 7 | 7 | 7 | 15 | 34 |
| | rB | 7 | 3 | 7 | 7 | 7 | 7 | 10 | 32 |
| | rC | 7 | 7 | 3 | 7 | 7 | 7 | 15 | 34 |

TABLE 1-continued

Parental and SCHEMA-derived chimeric HA1 subunits

| | Inherited block | | | | | | | |
|---|---|---|---|---|---|---|---|---|
| Protein | A | B | C | D | E | F | E | m |
| rD | 7 | 7 | 7 | 3 | 7 | 7 | 27 | 32 |
| rE | 7 | 7 | 7 | 7 | 3 | 7 | 28 | 32 |
| rF | 7 | 7 | 7 | 7 | 7 | 3 | 47 | 32 |

Inherited block: the numbers "7" and "3" represent the block origin. For example, rA comprises block A from the H3 protein and the remaining blocks all from the H7 protein.
E: the number of residue-residue contacts calculated by SCHEMA that would be broken upon block swapping relative to the closest parental protein.
m: the number of amino acid changes relative to the closest parental protein.

Example 2: Generation of the Full-Length HA Expression System

Figure 3A:
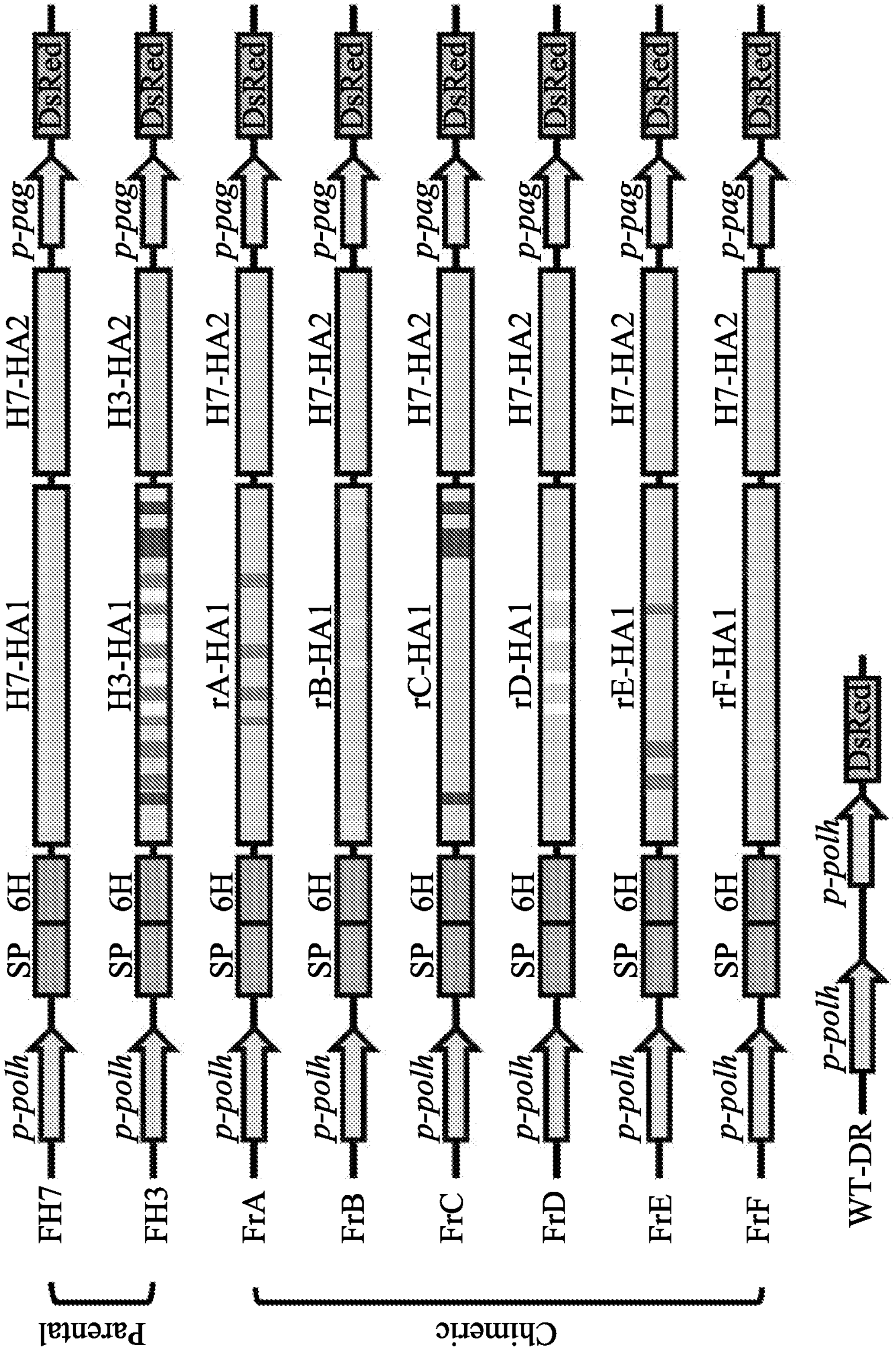
FIGS. 3A and 3B show the recombinant baculovirus constructions for the expression of parental and chimeric HA proteins in full length.

Since the bioactivity of the HA protein primarily relies on its trimeric conformation, the full-length chimeric HA constructs were generated by fusing the chimeric HA1 subunits with an HA2 subunit. The HA2 subunit from the H7 protein was employed and fused to the C-termini of the six chimeric HA1 subunits to form the full-length constructs (designated as FrA to FrF, respectively). The full-length parental constructs, FH7 and FH3, were constructed using their original HA1 and HA2 sequences, respectively (FIG. 3A). The full-length amino acid sequences of HA1 and HA2 sequences in the parental constructs FH7 and FH3 and the chimeric HA constructs FrA to FrF are represented by SEQ ID NOs: 9 to 16, respectively.

Further, the recombinant baculoviruses, vFH7, vFH3, and vFrA to vFrF, were generated for carrying the respective expression constructs (including 6H (histidine) tags) to express either the parental or one of the six chimeric full-length HAs by infecting insect Sf21 cells. WT-DR, a wild-type (WT) baculovirus expressing only the DsRed fluorescence protein, was also generated as a negative control (FIG. 3A).

Figure 3B:
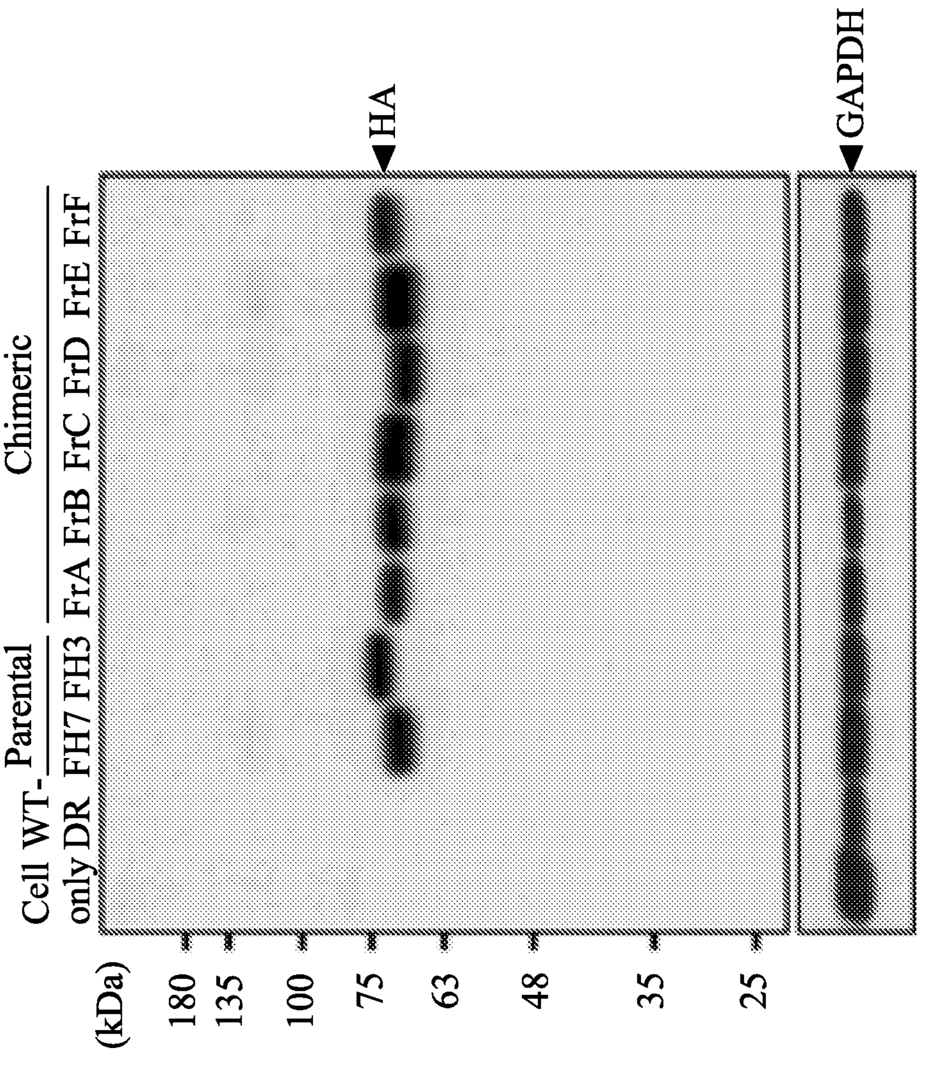

Recombinant protein expression was determined by Western blot analysis of infected Sf21 cell lysates, and all recombinant proteins (molecular weight about 70 kDa) could be detected by anti-His antibody. Non-infected cells or cells infected by the WT-DR virus exhibited no expression of HA proteins (FIG. 3B).

Figure 4A:
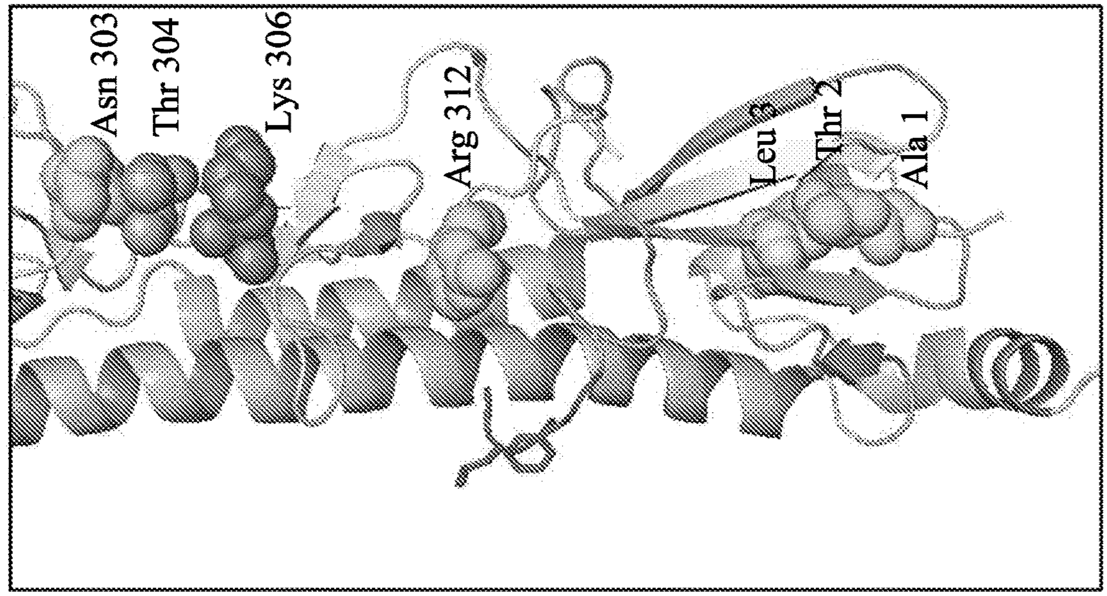
FIGS. 4A to 4D illustrate the 3D structures of different HA structural regions of the chimeric HA proteins.
Figure 4B:
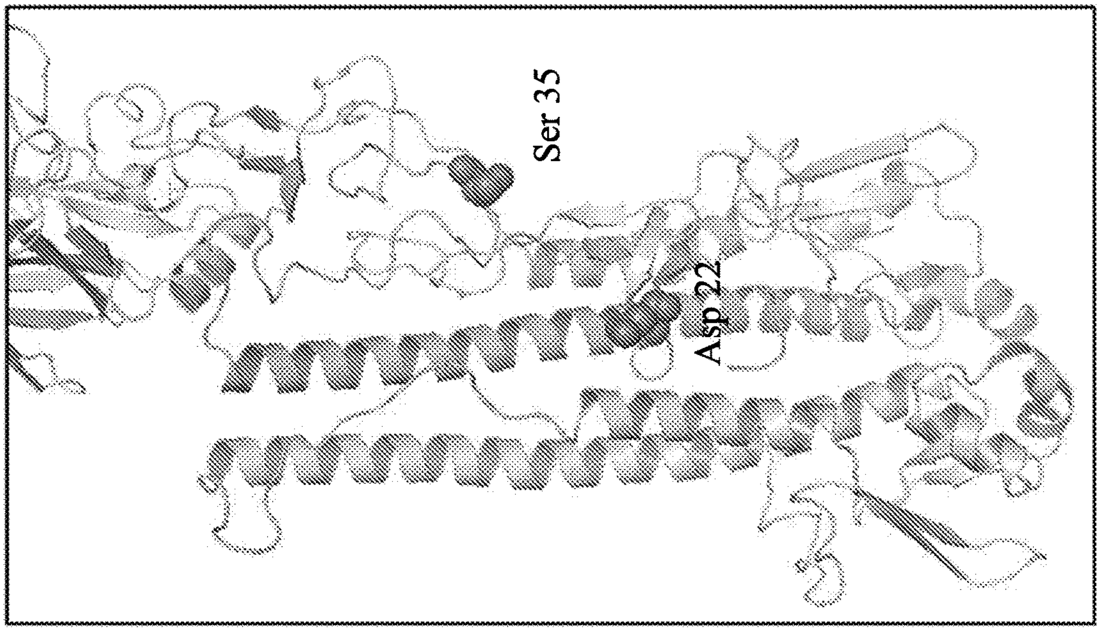
Figure 4C:
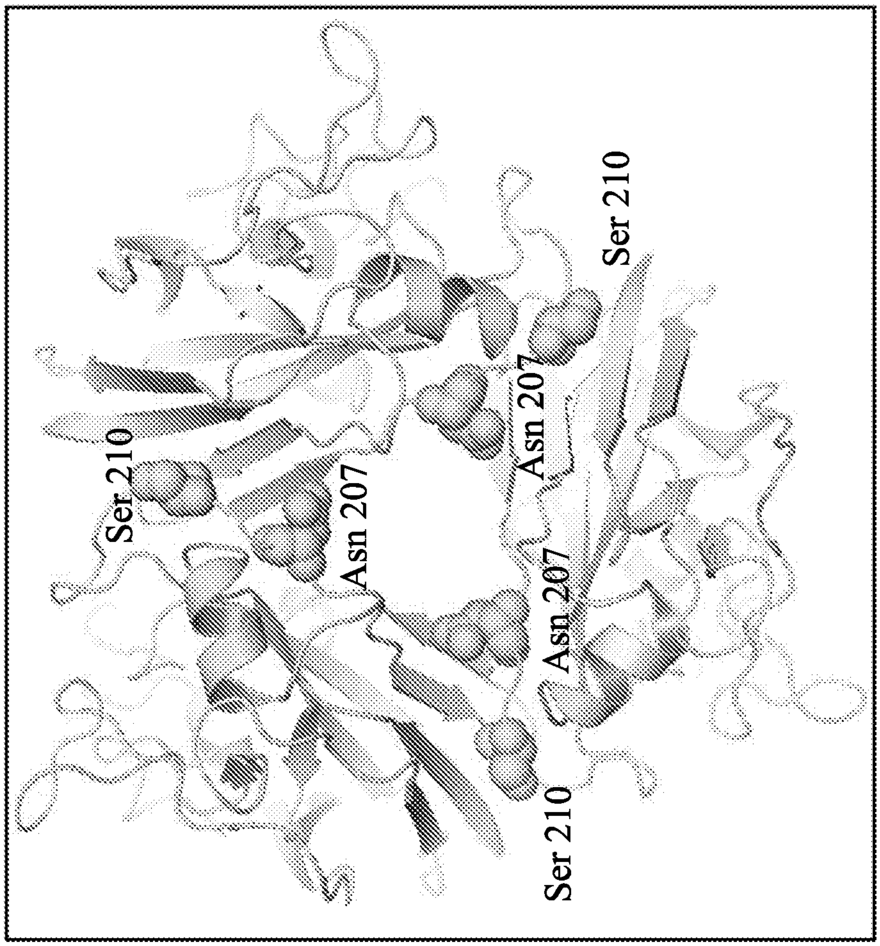
Figure 4D:
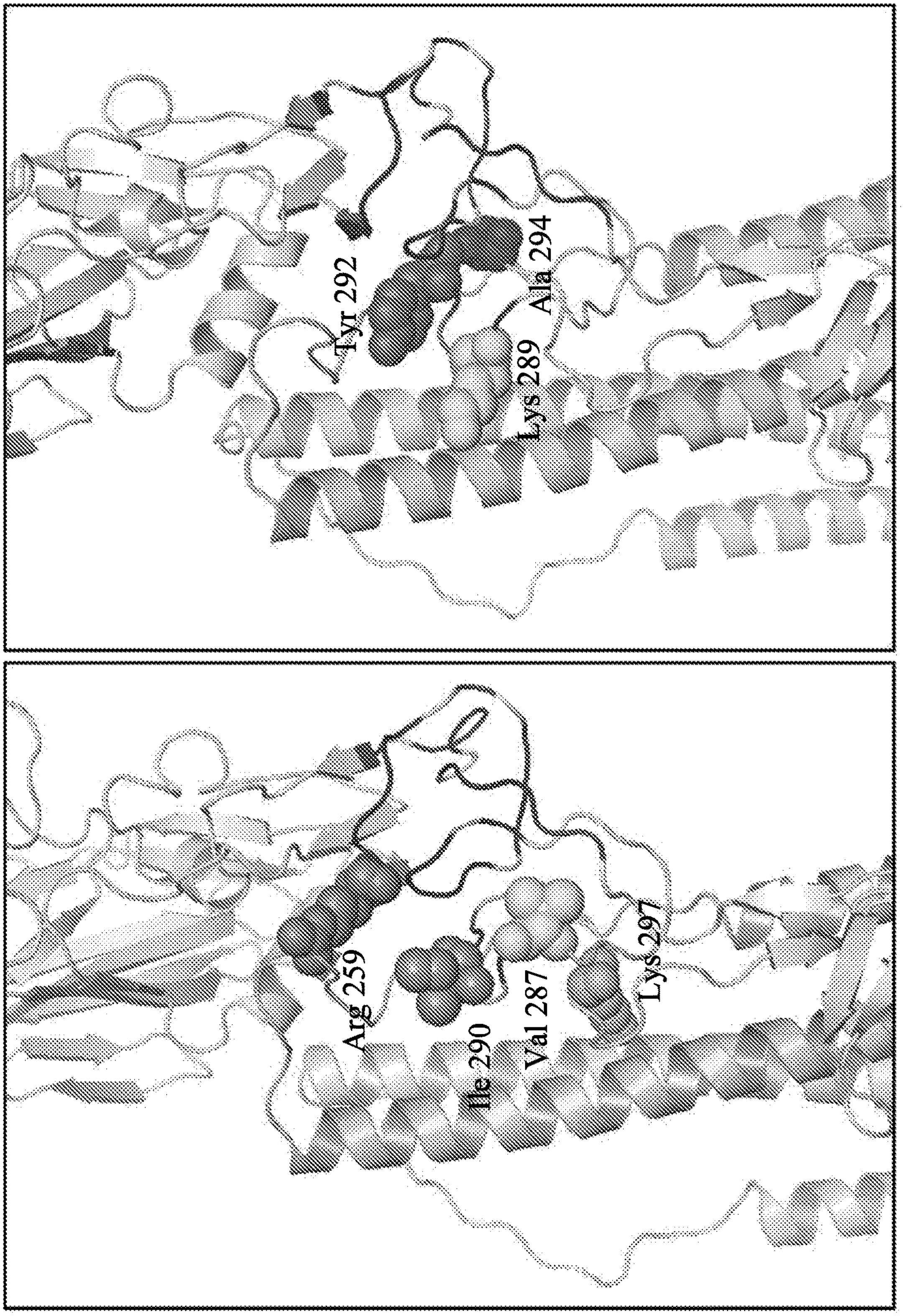

Referring to FIGS. 4A to 4D, the structural regions of the chimeric HA proteins containing amino acid residues relevant to chimera functions were defined. FIGS. 4A to 4C illustrated the fusion peptide pocket, the HA1 regions near the spring-loaded long coiled-coil helix of the HA2 subunit, and the HA1-HA1 interface of the FrB chimeric protein, while FIG. 4D illustrated the HA1-HA2 interface of the FrC chimeric protein. Key amino acids contributing to improved HA stability were indicated and labeled on the protein structures as shown in FIGS. 4A to 4D.

Figure 5:
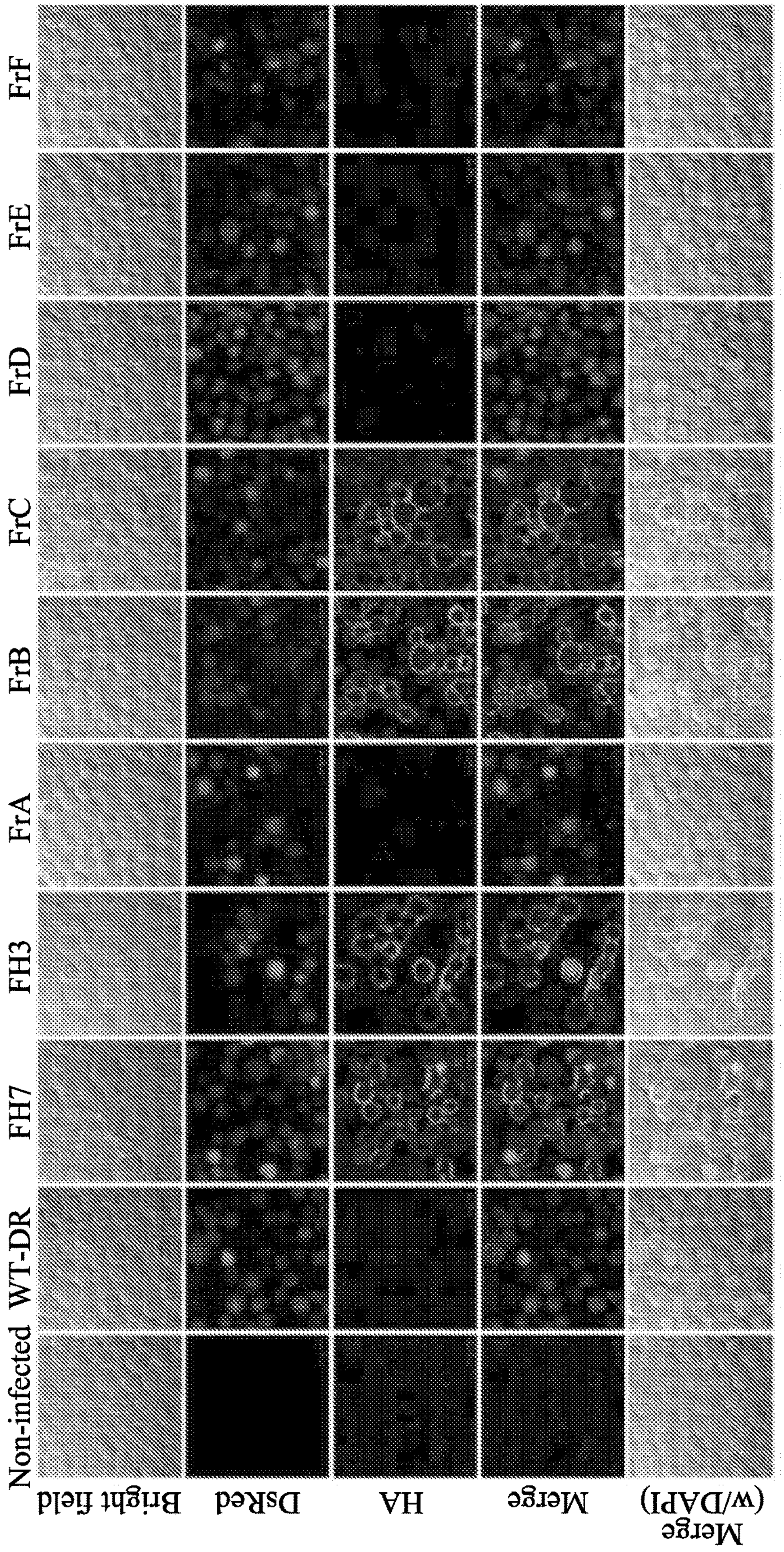
FIG. 5 shows the determination of cell-surface expression of HA constructs by immunofluorescence assay, wherein Sf21 cells infected by recombinant viruses with different HA constructs at MOI equal to 1 were fixed by 4% paraformaldehyde at 2 d.p.i., before HA proteins were stained by the primary anti-His antibody and secondary Alexa Fluor 488 antibody (green fluorescence). 4',6-diamidino-2-phenylindole (DAPI) staining (blue fluorescence) was used as a counterstain. Red fluorescence was from the DsRed reporter gene carried by the individual recombinant viruses.
Figure 6:
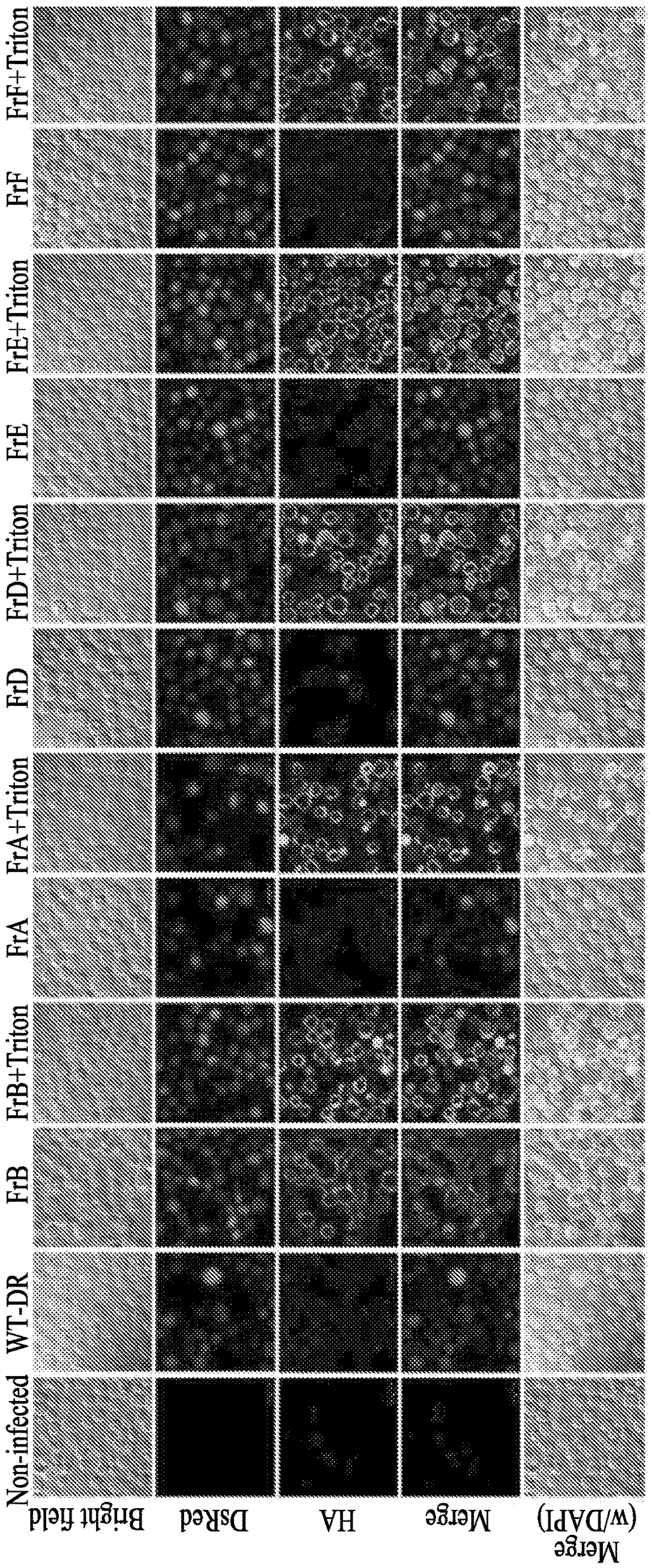
FIG. 6 shows the determination of the localization of FrA, FrD, FrE, and FrF by immunofluorescence assay, wherein Sf21 cells infected by the recombinant viruses expressing FrA, FrD, FrE, or FrF at MOI equal to 1 were fixed at 2 d.p.i., and half of the samples were permeabilized by 0.2% Triton. Localization of HA proteins was detected by the primary anti-His antibody and secondary Alexa Fluor 488 antibody (green fluorescence), with DAPI (blue fluorescence) as a counterstain. Proper red fluorescence expression from the DsRed reporter gene indicated successful virus infection.

The localization of the chimeric HA proteins in the cells was determined by immunofluorescence staining, and it was found that in addition to the two parental HAs, FrB and FrC could also be detected on the insect cell membrane (FIG. 5). Furthermore, upon permeabilizing cells by 0.2% Triton treatment, FrA, FrD, FrE, and FrF chimeric proteins could be detected inside cells by using the anti-His antibody (FIG. 6).

Example 3: Characterization and Bioactivity Assessments of Parental and Chimeric HA Proteins To determine whether the chimeric HA proteins preserved the HA conformation and bioactivity, the recognition by an H7-specific neutralizing monoclonal antibody (11082-R002, Sino Biological Inc., China)[13] of the HA constructs was determined in a cell-based ELISA assay. Since this monoclonal antibody neutralizes infection by an H7N9 influenza virus, it may recognize the viral structural epitope, and thus its reactivity to a chimeric protein indicates that the chimeric HAs are highly likely to preserve the functional HA structure and are more likely to elicit a functional antibody response upon immunization.

Figure 7:
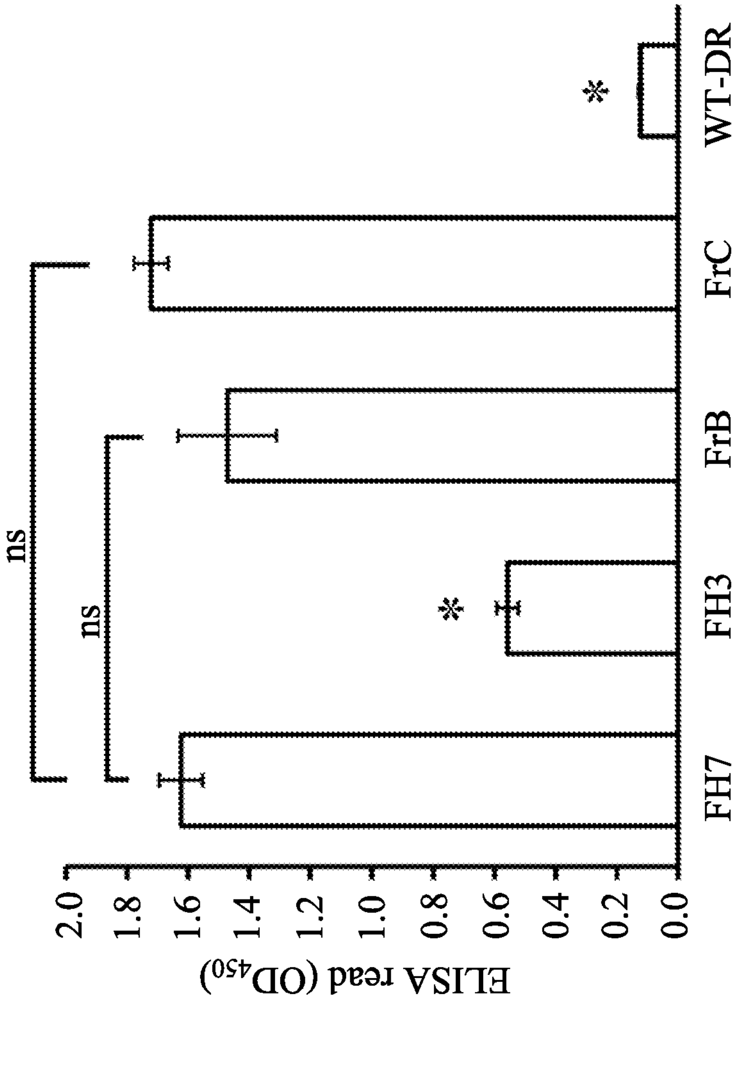
FIG. 7 shows the characterization of the chimeric HAs by H7 antibody recognition, wherein ELISA analysis revealed the Sf21 cells infected by baculoviruses expressing one of the HA constructs as antigens. Data are expressed as mean values±standard deviation (SD), representing three replicates from three independent experiments. * refers to the significant difference ($p<0.05$) versus the value of FH7; ns: not significant.

Sf21 cell samples membrane-permeabilized by 0.2% Triton treatment revealed that the H7-specific monoclonal antibody recognized FH7 and partially cross-reacted with FH3 (FIG. 7). Further, it was observed that FrB and FrC were recognized by this antibody to a degree comparable to FH7 (FIG. 7).

Figure 8A:
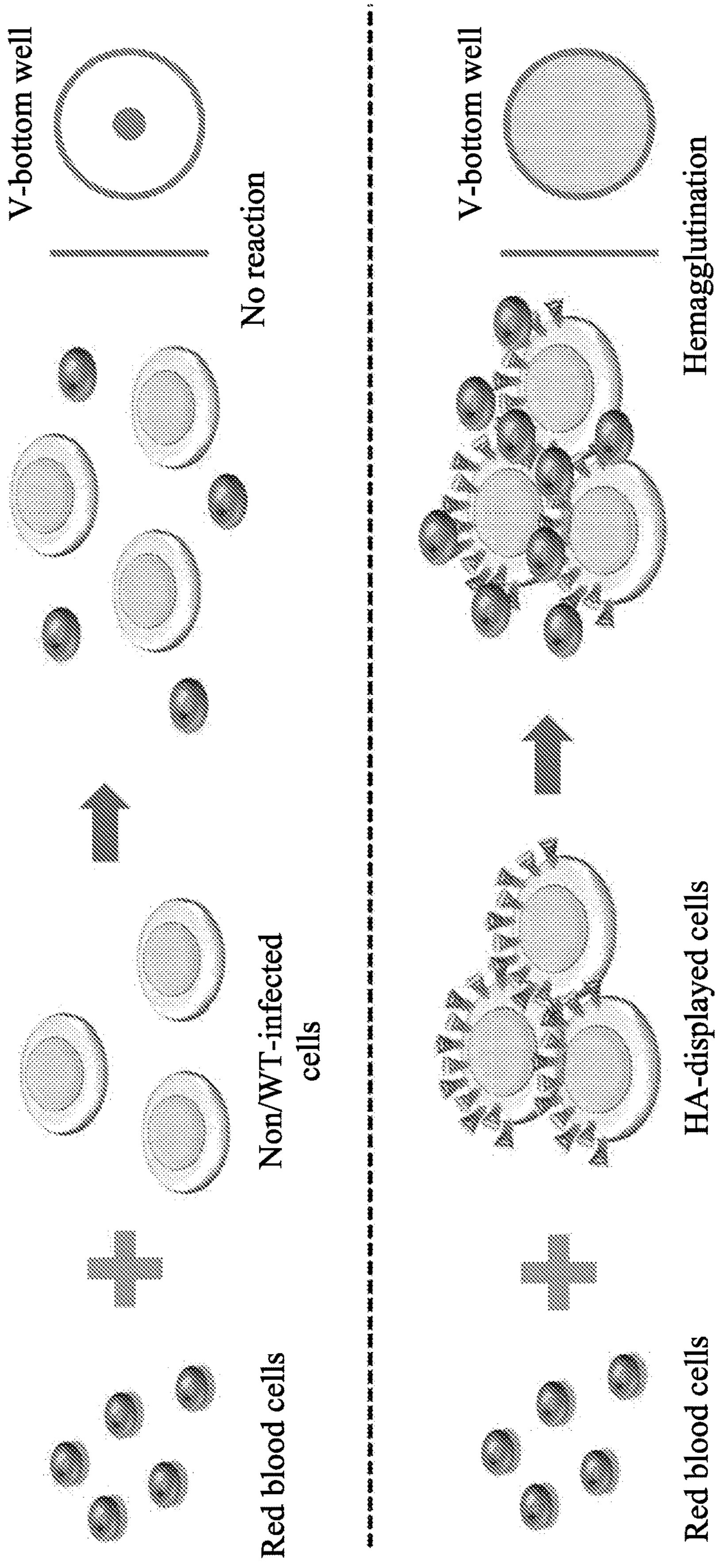
FIGS. 8A and 8B show the characterization of the chimeric HAs by the hemagglutination assay.
Figure 8B:
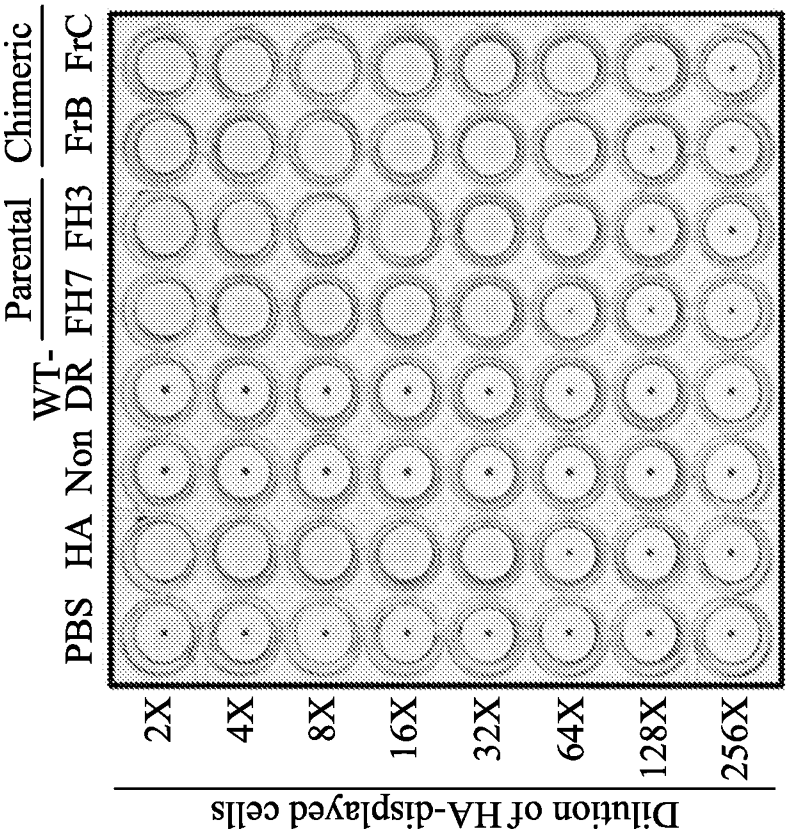

Moreover, the hemagglutination activity (a key feature of the HA protein) of the HA constructs was determined. First, Sf21 cells infected by recombinant viruses were disrupted by brief sonication to expose the cytosolic HAs. The disrupted cell suspensions were then serially 2-fold diluted and mixed with turkey red blood cells. If functional trimeric HAs exist in the disrupted cell suspensions, they would bind to the sialic acid receptors on the surfaces of the red blood cells and form clumps of red blood cell lattices[14, 15] (FIG. 8A). It was found that in addition to the cells expressing FrB, FrC could also agglutinate turkey red blood cells (FIG. 8B). These results suggest that FrB and FrC preserved the conformation and function of HA after recombination.

Example 4: Assay of Thermal Stability

To analyze the thermal stability of cell-expressed HAs, thermal hemagglutination assay protocols from other literature[8, 16] were adopted, which use loss of hemagglutination titer (HA titer) during heating to evaluate the thermal stability of HA proteins.

HA titers were initially determined for the infected cells, and then the cell amounts were adjusted to an HA titer of 64. The cells were incubated at 50° C. for different time periods and then cooled down to 4° C. for the hemagglutination assay.

Figure 9:
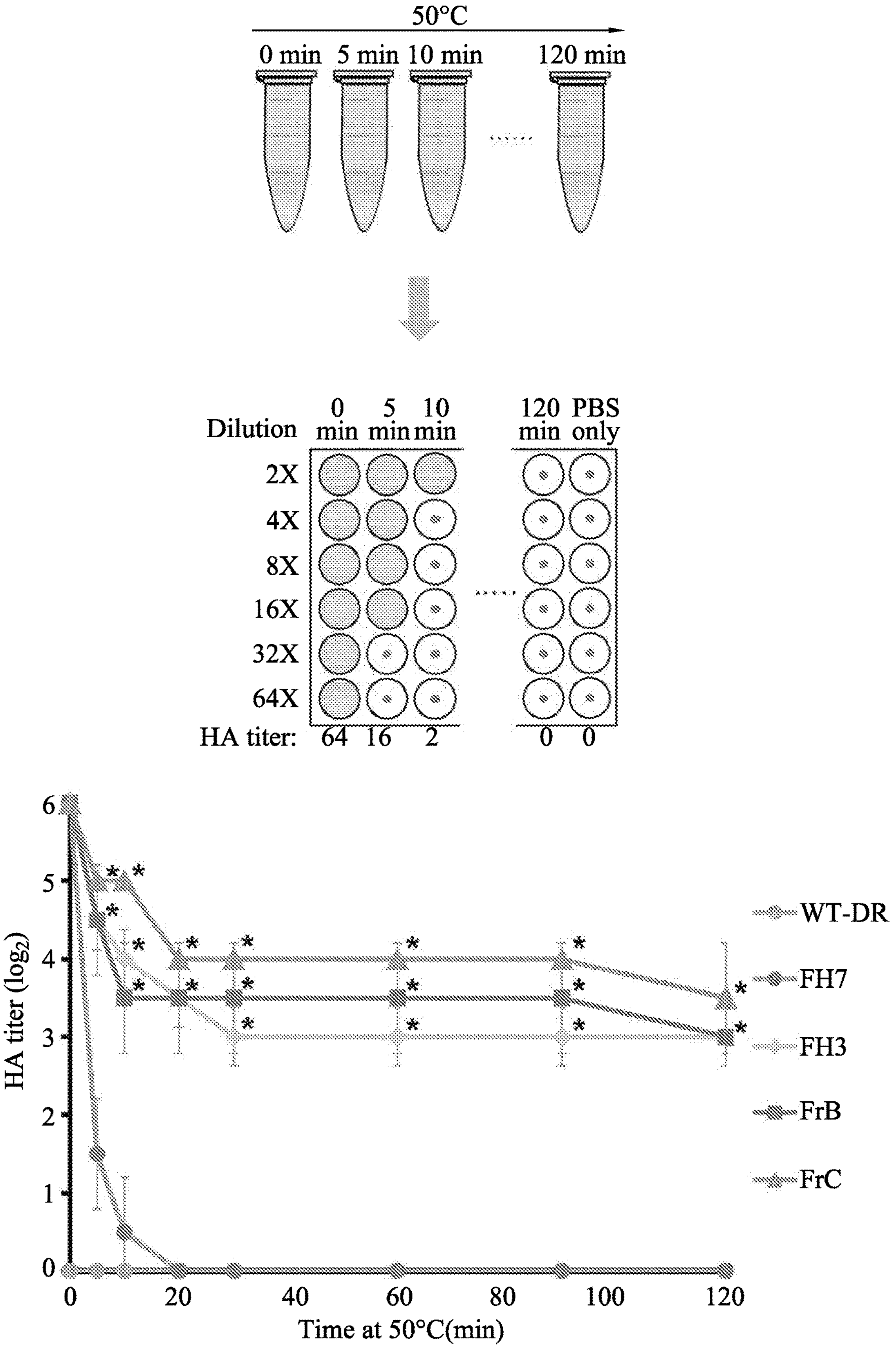
FIG. 9 shows the thermal hemagglutination assay to determine the stability of HAs, wherein Hi5 cells infected with different recombinant baculoviruses were prepared with an initial HA titer of 64, and incubated at 50° C. for the indicated time periods (0, 5, 10, 20, 30, 60, 90, and 120 minutes). After cooling down to 4° C., HA titers of cell samples were measured by the hemagglutination assay. Data are expressed as mean values±SD, representing three replicates from three independent experiments. * refers to significant difference ($p<0.05$) versus the titer of FH7 at each time point.

It was found that FH7 exhibited gradual loss of HA titer immediately upon starting the heating process and had completely lost its hemagglutination activity after 20 min of heating. The other parental sample, FH3, showed a gradual decrease of the hemagglutination activity for the initial 30 min of heating, but it retained the HA titer until the end of the 120-min experimental period. For cells expressing either FrB or FrC, HA titers decreased during the initial 10 to 20 min of heating but then maintained near constant titers toward the end of the heating process. Cells infected by WT-DR were used as a negative control and showed no HA titer during the experimental period (FIG. 9). These results suggest that the FrB and FrC proteins exhibit significantly enhanced stability at 50° C. compared to the parental FH7 protein.

Example 5: Assay of Eliciting Neutralizing Antibodies Against the H7N9 Virus

To explore if the chimeric HA proteins could still serve as efficient immunogens for triggering neutralizing antibodies against the H7N9 virus, the FH7, FrB, and FrC proteins were extracted from the infected insect cells to immunize mice, and their immune responses were further analyzed.

Figure 10A:
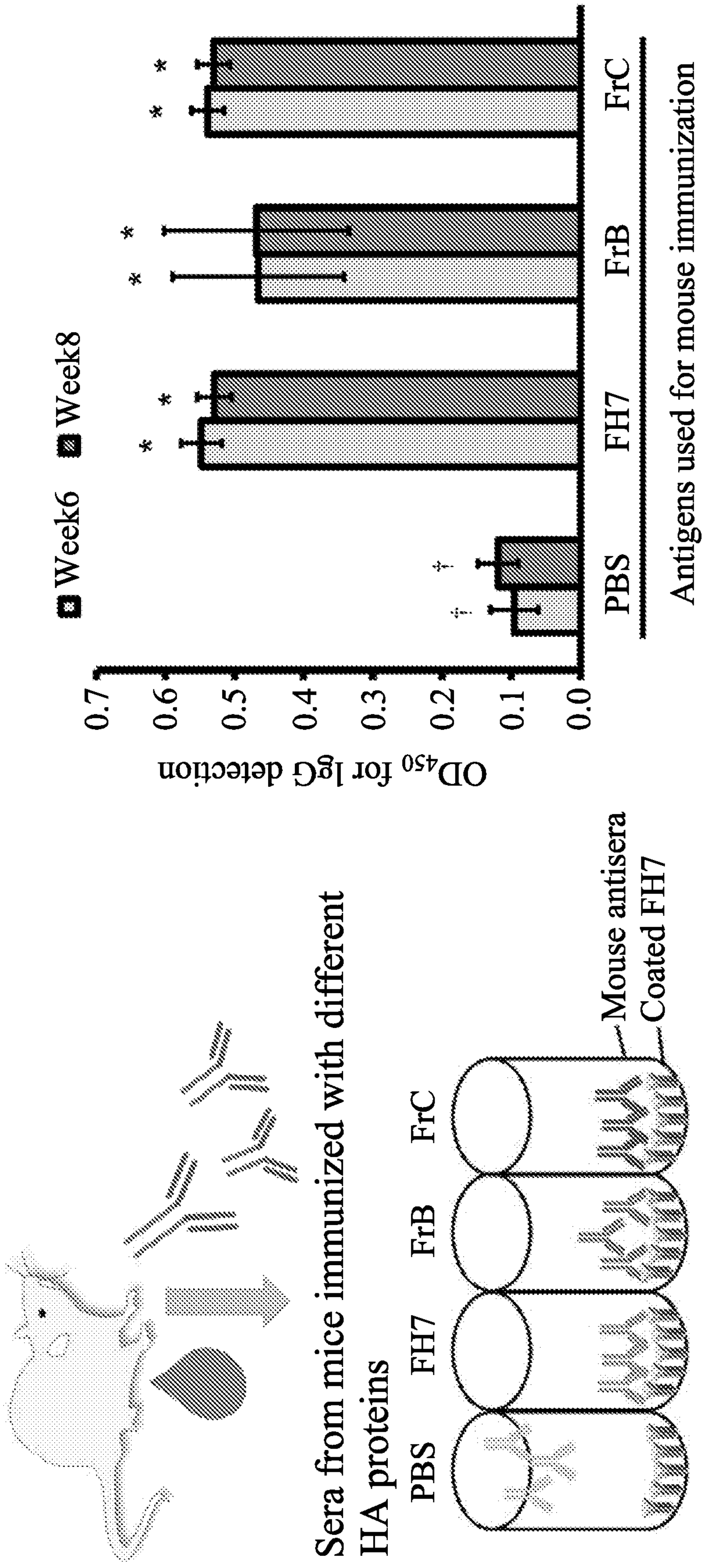
FIGS. 10A and 10B show that the antibodies elicited by FrB and FrC recognize an original FH7 antigen and inhibit H7N9 virus infection.

Three groups of five female BALB/c mice were immunized intraperitoneally with 30 μg of purified FH7, FrB, or FrC proteins, respectively. As negative controls, five mice were injected with PBS alone. Each mouse received two booster shots at week 2 and week 4 after primary immunization, and then the blood samples were collected at week 6 and week 8. The serum H7-specific IgG levels were determined by indirect ELISA using purified FH7 as an antigen (FIG. 10A). Mice immunized with FH7 protein showed a significantly higher H7-specific IgG antibody response on both week 6 and week 8 compared to the group immunized with PBS alone. Similarly, the groups immunized with either FrB or FrC showed levels of the H7-specific IgG response comparable to the FH7 group at these two time points (FIG. 10A).

Figure 10B:
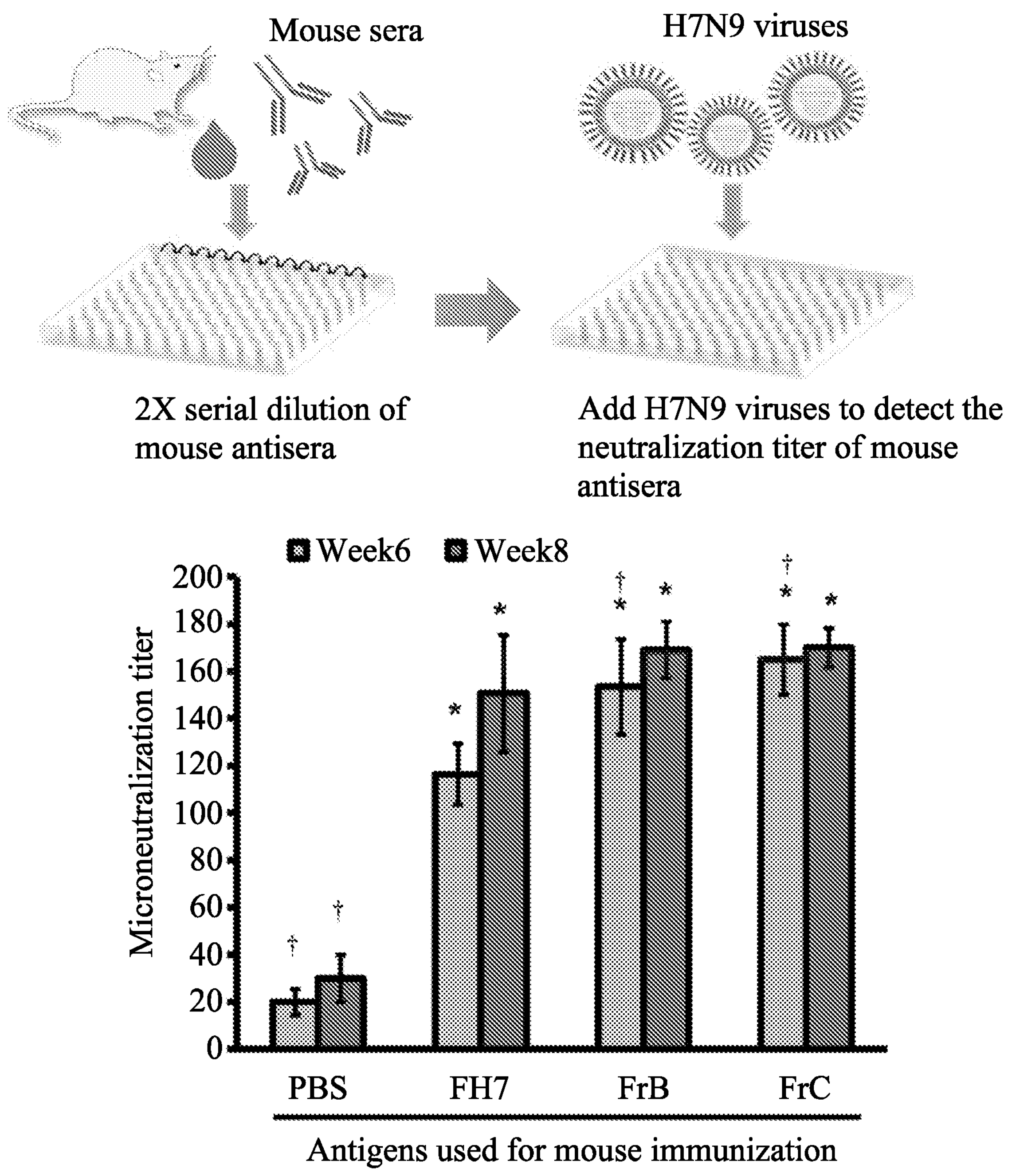

Further, a microneutralization assay was conducted to determine whether the immunized sera can neutralize real H7N9 influenza virus infection (FIG. 10B). H7N9 influenza viruses (the A/Taiwan/01/2013 strain) was incubated with serially diluted mouse sera, which were then used to infect Madin-Darby canine kidney (MDCK) cells. The microneutralization titer was determined at 3 d.p.i. as the reciprocal of the highest dilution without a virus-induced cytopathic effect (CPE). Sera from mice immunized with FrB or FrC presented a higher microneutralization titer compared to FH7-immunized sera at week 6 and a comparable titer at week 8. These data indicate that the chimeric HA proteins can elicit H7-specific antibodies that are able to inhibit H7N9 viral infection.

From the above, it can be seen that the recombinant chimeric proteins of the present disclosure generated from different influenza viruses by non-contiguous SCHEMA recombination have enhanced thermal stability, while maintaining proper antigenicity and high neutralizing efficiency.

It is known that homology of the parental proteins used in a SCHEMA approach affects the number of functional chimeras that can be derived. Nevertheless, even though the H7-HA1 and H3-HA1 sequences used in the present disclosure share only 38% sequence identity, the chimeric HA proteins are still expressed (FIG. 3B) and exhibit authentic HA function (i.e., sialic acid receptor binding), as assayed by the hemagglutination assay (FIG. 8B), implying that chimeric HA proteins can serve as better vaccine antigens to tackle H7N9 viruses.

Further, since the chimeric HA proteins of the present disclosure exhibit much higher thermal stability than FH7, they are more likely to support long-term storage and transportation as vaccine products.

While some of the embodiments of the present disclosure have been described in detail above, it is, however, possible for those of ordinary skill in the art to make various modifications and changes to the particular embodiments shown without substantially departing from the teaching and advantages of the present disclosure. Such modifications and changes are encompassed in the scope of the present disclosure as set forth in the appended claims.

REFERENCES

[1] WHO. (2018) Influenza (seasonal), World Health Organization.

[2] Mair, C. M., Ludwig, K., Herrmann, A., and Sieben, C. (2014) Receptor binding and pH stability—how influenza A virus hemagglutinin affects host-specific virus infection, Biochim. Biophys. Acta 1838, 1153-1168.

[3] Farnsworth, A., Cyr, T. D., Li, C., Wang, J., and Li, X. (2011) Antigenic stability of H1N1 pandemic vaccines correlates with vaccine strain, Vaccine 29, 1529-1533.

[4] Nakowitsch, S., Waltenberger, A. M., Wressnigg, N., Ferstl, N., Triendl, A., Kiefmann, B., Montomoli, E., Lapini, G., Sergeeva, M., Muster, T., and Romanova, J. R. (2014) Egg- or cell culture-derived hemagglutinin mutations impair virus stability and antigen content of inactivated influenza vaccines, Biotechnol. J. 9, 405-414.

[5] Nakowitsch, S., Wolschek, M., Morokutti, A., Ruthsatz, T., Krenn, B. M., Ferko, B., Ferstl, N., Triendl, A., Muster, T., Egorov, A., and Romanova, J. (2011) Mutations affecting the stability of the haemagglutinin molecule impair the immunogenicity of live attenuated H3N2 intranasal influenza vaccine candidates lacking NS1, Vaccine 29, 3517-3524.

[6] Weldon, W. C., Wang, B. Z., Martin, M. P., Koutsonanos, D. G., Skountzou, I., and Compans, R. W. (2010) Enhanced immunogenicity of stabilized trimeric soluble influenza hemagglutinin, PLOS One 5, e12466.

[7] Cotter, C. R., Jin, H., and Chen, Z. (2014) A single amino acid in the stalk region of the H1N1pdm influenza virus HA protein affects viral fusion, stability and infectivity, PLOS Pathog. 10, e1003831.

[8] Hanson, A., Imai, M., Hatta, M., McBride, R., Imai, H., Taft, A., Zhong, G., Watanabe, T., Suzuki, Y., Neumann, G., Paulson, J. C., and Kawaoka, Y. (2015) Identification of Stabilizing Mutations in an H5 Hemagglutinin Influenza Virus Protein, J. Virol. 90, 2981-2992.

[9] Gao, R., Cao, B., Hu, Y., Feng, Z., Wang, D., Hu, W., Chen, J., Jie, Z., Qiu, H., Xu, K., Xu, X., Lu, H., Zhu, W., Gao, Z., Xiang, N., Shen, Y., He, Z., Gu, Y., Zhang, Z., Yang, Y., Zhao, X., Zhou, L., Li, X., Zou, S., Zhang, Y., Li, X., Yang, L., Guo, J., Dong, J., Li, Q., Dong, L., Zhu, Y., Bai, T., Wang, S., Hao, P., Yang, W., Zhang, Y., Han, J., Yu, H., Li, D., Gao, G. F., Wu, G., Wang, Y., Yuan, Z., and Shu, Y. (2013) Human infection with a novel avian-origin influenza A (H7N9) virus, N. Engl. J. Med. 368, 1888-1897.

[10] Hu, Z., Jiao, X., and Liu, X. (2017) Antibody immunity induced by H7N9 avian influenza vaccines: evaluation criteria, affecting factors, and implications for rational vaccine design, Front. Microbiol. 8, 1898.

[11] Chao, Y. C., Lee, S. T., Chang, M. C., Chen, H. H., Chen, S. S., Wu, T. Y., Liu, F. H., Hsu, E. L., and Hou, R. F. (1998) A 2.9-kilobase noncoding nuclear RNA functions in the establishment of persistent Hz-1 viral infection, J. Virol. 72, 2233-2245.

[12] Naik, N. G., Lo, Y. W., Wu, T. Y., Lin, C. C., Kuo, S. C., and Chao, Y. C. (2018) Baculovirus as an efficient vector for gene delivery into mosquitoes, Sci. Rep. 8, 17778.

[13] Sun, X., Belser, J. A., and Tumpey, T. M. (2016) A novel eight amino acid insertion contributes to the hemagglutinin cleavability and the virulence of a highly pathogenic avian influenza A (H7N3) virus in mice, Virology 488, 120-128.

[14] Khurana, S., Verma, S., Verma, N., Crevar, C. J., Carter, D. M., Manischewitz, J., King, L. R., Ross, T. M., and Golding, H. (2011) Bacterial HA1 vaccine against pandemic H5N1 influenza virus: evidence of oligomerization, hemagglutination, and cross-protective immunity in ferrets, J. Virol. 85, 1246-743 1256.

[15] Matrosovich, M., and Klenk, H. D. (2003) Natural and synthetic sialic acid-containing inhibitors of influenza virus receptor binding, Rev. Med. Virol. 13, 85-97.

[16] Xu, S., Zhou, J., Liu, K., Liu, Q., Xue, C., Li, X., Zheng, J., Luo, D., and Cao, Y. (2013) Mutations of two transmembrane cysteines of hemagglutinin (HA) from influenza A H3N2 virus affect HA thermal stability and fusion activity, Virus Genes 47, 20-26.

[17] Pei, J., Kim, B. H., and Grishin, N. V. (2008) PROMALS3D: a tool for multiple protein sequence and structure alignments, Nucleic Acids Res. 36, 2295-2300.

[18] Yang, H., Carney, P. J., Chang, J. C., Villanueva, J. M., and Stevens, J. (2013) Structural analysis of the hemagglutinin from the recent 2013 H7N9 influenza virus, J. Virol. 87, 12433-12446.

[19] Yang, H., Carney, P. J., Chang, J. C., Guo, Z., Villanueva, J. M., and Stevens, J. (2015) Structure and receptor binding preferences of recombinant human A (H3N2) virus hemagglutinins, Virology 477, 18-31.

[20] Tung, H., Wei, S. C., Lo, H. R., and Chao, Y. C. (2016) Baculovirus IE2 stimulates the expression of heat shock proteins in insect and mammalian cells to facilitate its proper functioning, PLOS One 11, e0148578.

[21] Wei, S. C., Tsai, C. H., Hsu, W. T., and Chao, Y. C. (2019) Baculovirus IE2 interacts with viral DNA through Daxx to generate an organized nuclear body structure for gene activation in Vero cells, J. Virol. 93, e00149-00119.

[22] Bright, R. A., Carter, D. M., Crevar, C. J., Toapanta, F. R., Steckbeck, J. D., Cole, K. S., Kumar, N. M., Pushko, P., Smith, G., Tumpey, T. M., and Ross, T. M. (2008) Cross-clade protective immune responses to influenza viruses with H5N1 HA and NA elicited by an influenza virus-like particle, PLOS One 3, e1501.

What is claimed is:

1. A chimeric hemagglutinin (HA) protein comprising an HA1 subunit and an HA2 subunit, wherein the HA1 subunit is an amino acid sequence selected from the group consisting of SEQ ID NOs: 4 and 5 and the HA2 subunit is an HA2 subunit of an H7 subtype influenza virus.

2. A composition comprising the chimeric HA protein of claim 1 and a pharmaceutically acceptable carrier.

3. The composition according to claim 2, further comprising an adjuvant.

4. A method of inducing an immune response against an influenza virus in a subject in need thereof, comprising administering the composition according to claim 2 to the subject.

5. The method according to claim 4, wherein the influenza virus is influenza virus.

* * * * *